US012590941B1

(12) United States Patent
Whyte et al.

(10) Patent No.: US 12,590,941 B1
(45) Date of Patent: Mar. 31, 2026

(54) SYSTEMS AND METHODS FOR ENHANCED DETECTION AND QUANTIFICATION OF CHEMICAL SPECIES

(71) Applicant: Koloma, Inc., Denver, CO (US)

(72) Inventors: Colin Whyte, Grove City, OH (US);
Thomas Darrah, Westerville, OH (US);
Brent Lary, Columbus, OH (US);
Henry Wulsin, Columbus, OH (US);
Christopher Gardner, Columbus, OH
(US); William Eymold, Columbus, OH
(US); Jacob Harrington, Columbus,
OH (US)

(73) Assignee: Koloma, Inc., Denver, CO (US)

( * ) Notice: Subject to any disclaimer, the term of this
patent is extended or adjusted under 35
U.S.C. 154(b) by 0 days.

(21) Appl. No.: 18/943,706

(22) Filed: Nov. 11, 2024

(51) Int. Cl.
*G01N 33/28* (2006.01)
*B01D 53/00* (2006.01)
(Continued)

(52) U.S. Cl.
CPC ....... *G01N 33/2823* (2013.01); *B01D 53/002*
(2013.01); *B01D 53/025* (2013.01);
(Continued)

(58) Field of Classification Search
CPC .. G01N 33/2823; G01N 27/333; G01N 30/66;
G01N 2030/025; G01N 2030/524; B01D
53/002; B01D 53/025; B01D 53/265;
B01D 2256/16; B01D 2257/7025; B01D
2257/80
See application file for complete search history.

(56) References Cited

U.S. PATENT DOCUMENTS 4,718,921 A     1/1988 Makino
2008/0023328 A1*  1/2008 Jiang .................... G01N 27/308
                                        204/418
(Continued)

FOREIGN PATENT DOCUMENTS

WO        2022245440 A1    11/2022
WO     WO-2023192219 A1 * 10/2023   .......... H01J 49/0009

OTHER PUBLICATIONS

Korolev, A. A., et al. "Investigation of monolithic capillary columns
based on ethylene glycol dimethacrylate in gas chromatography."
Russian Journal of Physical Chemistry A 84 (2010): 1617-1622.
(Year: 2010).*

*Primary Examiner* — Robert J Eom
(74) *Attorney, Agent, or Firm* — K&L Gates LLP

(57) ABSTRACT

A method for enhanced mud gas logging includes receiving
a gas stream; separating the gas stream into a first gas
stream, a second gas stream, and a third gas stream; directing
the first gas stream to a gas chromatography configuration
including a gas chromatography column and a photoioniza-
tion detector; detecting, by the photoionization detector, gas
species in the first gas stream; separating, by a first separa-
tion component, water vapor from the second gas stream to
produce a processed second gas stream; detecting, by a first
mass spectrometer, gas species in the processed second gas
stream; separating, by a second separation component, water
vapor and other gas species from the third gas stream to
produce a processed third gas stream; and detecting, by a
second mass spectrometer, gas species in the processed third
gas stream.

18 Claims, 5 Drawing Sheets

(51) Int. Cl.

| | | |
|---|---|---|
| *B01D 53/02* | (2006.01) | |
| *B01D 53/26* | (2006.01) | |
| *G01N 27/333* | (2006.01) | |
| *G01N 30/02* | (2006.01) | |
| *G01N 30/52* | (2006.01) | |
| *G01N 30/66* | (2006.01) | |

(52) U.S. Cl.

CPC ......... *B01D 53/265* (2013.01); *G01N 27/333* (2013.01); *G01N 30/66* (2013.01); *B01D 2256/16* (2013.01); *B01D 2257/7025* (2013.01); *B01D 2257/80* (2013.01); *G01N 2030/025* (2013.01); *G01N 2030/524* (2013.01)

(56) References Cited

U.S. PATENT DOCUMENTS

| | | | | |
|---|---|---|---|---|
| 2009/0259080 | A1 | 10/2009 | Raman | |
| 2013/0233057 | A1* | 9/2013 | Karoum | ................ G01N 21/72 |
| | | | | 73/31.07 |
| 2015/0153314 | A1* | 6/2015 | Karoum | ................ G01N 30/46 |
| | | | | 73/23.36 |
| 2023/0393114 | A1 | 12/2023 | Darrah | |

* cited by examiner

SYSTEMS AND METHODS FOR ENHANCED DETECTION AND QUANTIFICATION OF CHEMICAL SPECIES

FIELD OF THE INVENTION

Embodiments of the present disclosure relate generally to the field of energy extraction, geochemistry, geology, or geophysics. More particularly, the present disclosure relates to methods for measuring, quantifying, and evaluating chemical species in fluids during the drilling of a well (e.g., mud gas logging), drill stem testing, formation testing, or other production testing (e.g., during or after the drilling of a well or borehole) of a well, or during the monitoring of fluid production from the well or borehole. Other embodiments disclose methods for monitoring and quantifying the composition of hydrogen, helium, ammonia, hydrocarbon gases, nitrogen, carbon dioxide, other gases, and hydrogen derivatives during the gathering, purification, and handling of these compounds.

BACKGROUND

This section is intended to introduce terminology and context associated with embodiments described in this disclosure. Thus, the following discussion in this section provides a framework for better understanding the disclosure, and is not to be viewed as an admission of prior art.

Hydrogen is a carbon-free energy carrier and chemical feedstock that can supplant carbon-based fossil fuels, especially when combined with other sources. Hydrogen can be generated using sustainable energy sources such as geothermal, solar, wind, and hydroelectric power. The disclosure herein relates to hydrogen produced from or generated within the Earth's subsurface and extracted by drilling, boring, mining, or various other means of penetrating the earth.

In the production of natural resources from formations within the earth, a well or borehole is drilled into the earth to the location where the natural resource is believed to be located. These natural resources may be hydrogen, helium, carbon dioxide, nitrogen, dihydrogen sulfide, methane, or other hydrocarbon gases; a dihydrogen sulfide reservoir, a hydrogen reservoir, a helium reservoir, a carbon dioxide reservoir, a natural gas reservoir, a reservoir rich in dihydrogen sulfide, a reservoir rich in hydrocarbons, a reservoir rich in hydrogen, a reservoir rich in helium; the natural resource may be fresh water, brackish water, or brine; it may be a heat source for geothermal energy; or it may be some other natural resource, ore deposit, mineral, metal, or gem that is located within the ground.

These resource-containing formations may be a few hundred feet, a few thousand feet, or tens of thousands of feet below the surface of the earth, including under the floor of a body of water (e.g., below the sea floor) or beneath other natural resources (e.g., below aquifers, lakes, mines). In addition to being at various depths within the earth, these formations may cover areas of differing sizes, shapes, and volumes.

Typically, and by way of general illustration, in drilling a well an initial borehole is made into the earth (e.g., the surface of land or seabed), and then subsequent and smaller diameter boreholes are drilled to extend the overall depth of the borehole. In this manner as the overall borehole gets deeper its diameter becomes smaller, resulting in what can be envisioned as a telescoping assembly of holes with the largest diameter hole being at the top of the borehole closest to the surface of the earth.

Thus, by way of example, the starting phases of a subsea drill process may be explained in general as follows. Once the drilling rig is positioned on the surface of the water over the area where drilling is to take place, an initial borehole is made by drilling a 36" hole in the earth to a depth of about 200-300 ft. below the seafloor. A 30" casing is inserted into this initial borehole. This 30" casing may also be called a conductor. The 30" conductor may or may not be cemented into place. During this drilling operation a riser is generally not used and the cuttings from the borehole (e.g., the earth and other material removed from the borehole by the drilling activity) are returned to the seafloor. Next, a 26" diameter borehole is drilled within the 30" casing, extending the depth of the borehole to about 1,000-1,500 ft. This drilling operation may also be conducted without using a riser. A 20" casing is then inserted into the 30" conductor and 26" borehole. This 20" casing is cemented into place. The 20" casing has a wellhead secured to it. (In other operations an additional smaller diameter borehole may be drilled, and a smaller diameter casing inserted into that borehole with the wellhead being secured to that smaller diameter casing.) A blow out preventer (BOP) is then secured to a riser and lowered by the riser to the sea floor, where the BOP is secured to the wellhead. From this point forward, all drilling activity in the borehole takes place through the riser and the BOP.

It should be noted that subsea drilling operations that do not employ a riser are also contemplated.

For a land-based drill process, the steps are similar, although the large diameter tubulars, 30"-20" are typically not used. Thus, and generally, there is a surface casing that is typically about 13⅜" diameter. This may extend from the surface, (e.g., wellhead and BOP) to depths of tens of feet to hundreds of feet. One of the purposes of the surface casing is to meet environmental requirements to protect groundwater by preventing surface casing ventflow to groundwater aquifers or prevent surface casing ventflow of greenhouse gases or flammable gases to groundwater aquifers or the atmosphere. The surface casing should have a sufficiently large diameter to allow the drill string, production equipment (e.g., electrical submersible pumps (ESPs)), and circulation mud to pass through. Below the casing, one or more different diameter intermediate casings may be used. (It is understood that sections of a borehole may not be cased and are referred to as open hole.) These can have diameters in the range of about 9" to about 7", although larger and smaller sizes may be used, and can extend to depths of thousands and tens of thousands of feet.

The section of the well located within the reservoir (i.e., the section of the formation containing the natural resources being targeted) can be called the pay zone. The production tubing is placed inside the casing and extends from a pay zone, or production zone of the borehole, up to and through the wellhead on the surface. There may be a single production tubing or multiple production tubings in a single borehole, with each of the production tubing endings being at different depths.

Fluid communication between the formation and the well or borehole can be greatly increased by the use of perforations, hydraulic fracturing, or other stimulation techniques. The first uses of hydraulic fracturing date back to the late 1940s and early 1950s. In general, hydraulic fracturing treatments involve forcing fluids down the well or borehole and into the formation, where the fluids enter the formation and crack, e.g., by forcing the layers of rock to break apart or fracture. These fractures create channels or flow paths that may have cross sections of a few microns, to a few millimeters, to several millimeters in size, and potentially larger. The fractures may also extend out from the well in all directions for a few feet, several feet, and tens of feet or further. The fractures may be kept open by using a proppant (e.g., various sized sand or other mineral grains) that is forced down the well with the fracturing fluid in a single operation. It should be remembered that the longitudinal axis of the well or borehole in the reservoir may not be vertical: it may be on an angle (either sloping up or down) or it may be horizontal.

During the drilling of wells or boreholes, drilling fluids (i.e., water-based mud, oil-based mud, water, foam, aerated mud, air, synthetic fluids, or other fluids), herein referred to as "drilling fluid," is often pumped down the borehole through the drill string and out into the borehole at the drill bit, then back up to the surface between the exterior of the drill string and the borehole wall. In some drilling operations, air or aerated fluid is injected through the drill string in a similar manner and can return formation fluids, including gases, to the surface. In the case where drilling fluid is used, it can lubricate the borehole, drill bit, and drill string, and prevent thermal degradation of the drill bit, as well as provide a medium through which to eject drilled rock (e.g., cuttings), sediment material, or formation fluids (e.g., gases) up the borehole to the surface.

Within the rock or sediment being drilled, fluids stored in pore spaces or fractures in the subsurface at the point of contact with or around the drill bit, or in shallower intervals that now are in contact with the borehole, can enter and mix with the circulating drilling fluid and return to the surface. Subsurface fluids, including gas, that enter the drilling fluid can remain dissolved in the circulating drilling fluid, migrate buoyantly as bubbles through the column of drilling fluid, or if sufficiently pressurized can flow as pulses of gas up the well or borehole.

At the surface, fluids, including gas, and the drilled rock or sediment material may be separated from the drilling fluid. The drilled rock or sediment material may be dropped onto a vibrating screen (shaker) to separate the solid material from drilling fluid, which may or may not be recycled and pumped back down the borehole during ongoing drilling of the borehole. During this time, formation fluids, including gas, may be separated from the drilling fluid, often using an agitating device, commonly termed the agitator, and the formation fluids (i.e., including gas) may be sampled directly using various sample devices (e.g., stainless steel cylinders, Isotubes®, Isobags®, Isoflasks®, copper tubes, etc.), plumbed to a gas buster or flaring device, or plumbed using piping or tubing (e.g., polyethylene, copper, or steel) to gas meters and/or various chemical instruments that can measure the bulk concentrations of various gas species separated from the drilling fluid.

The instrumentation used to quantify the bulk concentrations of gases separated from the drilling fluid may include a gas flow meter, a gas chromatograph, a mass spectrometer, or other form of optical (e.g., LiDAR, laser Raman spectroscopy) sensor, or combinations thereof.

Air drilling or aerated drilling are processes of drilling with compressed air (i.e., either as the fluid medium (air drilling) or with air aerosolized in the drilling fluid to lighten drilling fluid weight) and to help facilitate the return of drilled rock (i.e., cuttings), sediment material, or formation fluids (e.g., gases, hydrocarbon liquids, or other formation fluids, such as brines) up the borehole instead of using a fluid-based mud system (e.g., oil or water-based mud system). The air or aerated fluids that return to the surface can also be plumbed to chemical instrumentation by various forms of piping or tubing (e.g., polyethylene, copper, or steel) and may be measured or sampled using similar instrumentation, although without requiring an agitator as is used in fluid-based mud systems.

In some examples, the subsurface rock formation from which gases are extracted can include at least one of sedimentary rocks (e.g., sandstone, limestone, shales, graywacke, evaporites), metamorphic rocks (e.g., gneisses, marbles), igneous rocks (e.g., dunite, pyroxenite, basalt, gabbros, granites, or other igneous rocks), or formations containing overly thermally mature hydrocarbon fluids, hydrocarbon source rocks, coal, or graphite. Other examples can include iron-rich rock, mafic igneous rock, metamorphosed or hydrothermally altered mafic igneous rock, olivine- or pyroxene-bearing igneous, metamorphic, or sedimentary rock or sediment, metamorphosed or hydrothermally altered olivine- or pyroxene-bearing igneous, metamorphic, or sedimentary rock or sediment, serpentine mineral-bearing rock or sediment, partially or completely serpentinized rock, serpentinite, pyrite, iron-rich sandstone, other iron-rich sedimentary rock, or iron-rich sediments.

In some examples, the source of hydrogen can include any of the sources described above (e.g., mafic or ultramafic rock) that is drilled, drilled and stimulated (e.g., hydraulic fracturing or perforation), drilled and stimulated (e.g., hydraulic fracturing or perforation) with the accompanying introduction of heat, chemicals, or fluids (e.g., carbon dioxide, dihydrogen sulfide), or fluids encountered while interacting with various subsurface reservoirs or geothermal systems, mining operations, water well drilling, formation waters, or any fluids exsolved from processes related to their exploration, characterization, or extraction.

BRIEF SUMMARY

Currently available systems and methods have limited capacity to accurately measure or quantify key components related to hydrogen or helium exploration, and (as described below) are not optimized for more traditional mudlogging purposes including hydrocarbon exploration. Currently available systems and methods are not able to robustly detect and/or quantify hydrogen, key hydrogen derivatives such as ammonia, water vapor, hydrogen cyanide, water isotopes or others. Similarly, currently available systems and methods are not able to robustly detect and/or quantify helium or other noble gases. Further, these systems can produce inaccurate results for compounds such as nitrogen, carbon dioxide, and other hydrocarbons compared to the anticipated higher analytical precision and accuracy that can be achieved in the laboratory setting. Moreover, in some instances, the currently disclosed analytical methods do not utilize suitable sample preparation systems or methods capable of detecting and measuring these compounds within the analytical precision and accuracy tolerance of commercial chemical instruments.

There exists a need for enhanced systems and methods for measuring and quantifying gases collected from a wellbore, particularly in connection with hydrogen or helium exploration. The disclosure herein provides example embodiments of systems and methods that address this need, among others. Accordingly, some examples are specific to the exploration for geologic hydrogen, geothermal energy, helium, ammonia, hydrocarbon gases, nitrogen, carbon dioxide, other gases, and various hydrogen-derived chemical species (e.g., dihydrogen sulfide, hydrogen cyanide) in fluids during the drilling of a well or borehole (e.g., mud gas logging). Other embodiments relate to measurements of similar fluids during well or borehole testing (e.g., drill stem testing, formation testing, flow testing, or other production testing of subsurface fluids) during or after the drilling of a well or borehole, during the monitoring of fluid production from the well or borehole, or the measurement and quantification of these chemical species during the gathering, purification, and handling of fluids obtained from or synthesized in the subsurface. Embodiments include the devices and processes for the measurement of these components in these various processes.

In one example embodiment, a method is provided for enhanced mud gas logging. The method includes: receiving a gas stream; separating the gas stream into a first gas stream, a second gas stream, and a third gas stream; directing the first gas stream to a gas chromatography configuration including a gas chromatography column and a photoionization detector; detecting, by the photoionization detector, gas species in the first gas stream; separating, by a first separation component, water vapor from the second gas stream to produce a processed second gas stream; detecting, by a first mass spectrometer, gas species in the processed second gas stream; separating, by a second separation component, water vapor and other gas species from the third gas stream to produce a processed third gas stream; and detecting, by a second mass spectrometer, gas species in the processed third gas stream.

In another example embodiment, a chemical instrumentation system is disclosed herein for measuring gases collected from a wellbore. The chemical instrumentation system includes gas stream tubing, a gas chromatography configuration, and a mass spectrometer configuration. The gas stream tubing is configured to receive a gas stream from the wellbore and split the gas stream into a first gas stream, a second gas stream, and a third gas stream. A gas chromatography configuration is coupled to the first gas stream. The gas chromatography configuration includes a gas chromatography column configured to receive a subset of the first gas stream, and a photoionization detector coupled to the gas chromatography column and configured to quantify gas species eluted from the gas chromatography column. The chemical instrumentation system further includes a mass spectrometer configuration. The mass spectrometer configuration includes a first separation component coupled to the second gas stream and configured to separate water vapor from the second gas stream to produce a processed second gas stream, and a first mass spectrometer configured to measure species of the processed second gas stream. The mass spectrometer configuration further includes a second separation component coupled to the third gas stream and configured to separate water vapor and additional gas species from the third gas stream to produce a processed third gas stream, and a second mass spectrometer configured to measure species of the processed third gas stream.

In another example embodiment, a method is provided for identifying drill bit metamorphism in a wellbore. The method includes collecting a gas sample from the wellbore, generating a profile of the gas sample, the profile indicating abundances of gases in the gas sample, and identifying, based on the abundances of the gases in the gas stream, artificial generation of a particular gas in the fluid or gas sample.

In yet another example embodiment, a method is provided for enhanced quantification of geologic hydrogen in a gas stream from a wellbore. This method includes receiving a gas stream from the wellbore, quantifying an amount of geologic hydrogen in the gas stream, quantifying an amount of geologic hydrogen derivatives in the gas stream, correlating the amount of geologic hydrogen derivatives in the gas stream to an estimated amount of source hydrogen, and generating the enhanced quantification of geologic hydrogen in the gas stream based on the amount of hydrogen in the gas stream and the estimated amount of source hydrogen.

In some embodiments, the geologic hydrogen derivatives include ammonia, and the method further includes: quantifying an amount of ammonium in the mud fluid stream; and measuring an amount of ammonia present in the gas stream. Quantifying the amount of geologic hydrogen derivatives in the gas stream is based on the amount of ammonium in the mud fluid stream and the amount of ammonia present in the gas stream. In some embodiments, quantifying the amount of ammonium in the mud fluid stream includes applying an ion-selective electrode probe to the mud fluid stream to measure the amount of ammonium.

In some embodiments, the method further includes separating methane from the gas stream, and measurement of the amount of ammonia present in the gas stream occurs after separating methane from the gas stream. In other embodiments, the method further includes separating water vapor from the gas stream, and measurement of the amount of ammonia present in the gas stream occurs after separating water vapor from the gas stream. In still further embodiments, the method includes separating a water isotope from the gas stream, and measurement of the amount of ammonia present in the gas stream occurs after separation the water isotope from the gas stream.

In some embodiments, the geologic hydrogen derivatives include ammonia, hydrogen cyanide, dihydrogen sulfide, one or more hydrocarbons, or a combination thereof. In other embodiments, the geologic hydrogen derivatives include water, a water isotope, or a combination thereof.

In some embodiments, the step of quantifying an amount of geologic hydrogen derivatives in the gas stream includes directing the gas stream to a gas chromatography column and a thermal conductivity detector. The gas chromatography column may be packed with, for example, ethylene glycol-dimethacrylate.

In a further embodiment, a chemical instrumentation system for enhanced quantification of geologic hydrogen in a gas stream from a wellbore is provided. The chemical instrumentation system includes gas stream tubing, a gas chromatography configuration, and a computing device. The gas stream tubing configured to: receive a mud fluid stream from the wellbore, wherein the mud fluid stream includes geologic hydrogen and geologic hydrogen derivatives and split a gas stream from the mud fluid stream. The gas chromatography configuration is coupled to the gas stream and includes a gas chromatography column configured to receive the gas stream and one of a thermal conductivity detector or a photoionization detector coupled to the gas chromatography column and configured to quantify gas species eluted from the gas chromatography column. The gas species includes the geologic hydrogen and the geologic hydrogen derivatives. The computing device has a processor and memory storage operably coupled to the processor, and the memory storage has one or more computer programming routines. The processor is configured to read and execute the one or more computer programming routines, which include machine readable and executable instructions to: quantify an amount of geologic hydrogen in the gas stream; quantify an amount of geologic hydrogen derivatives in the gas stream;

7 correlate the amount of geologic hydrogen derivatives in the gas stream to an estimated amount of source hydrogen; and generate the enhanced quantification of hydrogen in the gas stream based on the amount of geologic hydrogen in the gas stream and the estimated amount of source hydrogen.

In further embodiments, the gas chromatography configuration includes a separation component coupled to the gas stream and configured to separate water vapor from the gas stream prior to measuring the gas species of the gas stream.

In still further embodiments, the geologic hydrogen derivatives include ammonia, hydrogen cyanide, dihydrogen sulfide, one or more hydrocarbons, water, water isotopes, or combinations thereof.

In some embodiments, the geologic hydrogen derivatives include ammonia, and the one or more computer programming routines further include machine readable and executable instructions to: quantify an amount of ammonium in the mud fluid stream; and measure an amount of ammonia present in the gas stream. Quantifying the amount of geologic hydrogen derivatives in the gas stream is based on the amount of ammonium in the mud fluid stream and the amount of ammonia present in the gas stream.

In some aspects, the chemical instrumentation system further includes an ion-selective electrode probe. Quantifying the amount of ammonium in the mud fluid stream may include receiving a measurement of the amount of ammonium from the ion-selective electrode probe applied to the mud fluid stream.

In a still further aspect, the gas chromatography configuration includes a separation component coupled to the gas stream and configured to separate methane from the gas stream prior to measuring the ammonia present in the gas stream.

In a still further embodiment, a method for automatic correction of gas species quantification includes: receiving a gas stream; separating the gas stream into a first gas stream and a second gas stream; directing the first gas stream to a first chemical instrumentation system; receiving first data from the first chemical instrumentation system, the first data indicating a first quantity of a first gas species in the first gas stream; directing the second gas stream to a second chemical instrumentation system; receiving second data from the second chemical instrumentation system, the second data indicating a second quantity of a second gas species in the second gas stream; automatically determining a signal correction factor based on the first quantity of the first gas species in the first gas stream; and applying the signal correction factor to the second data to produce a refined second dataset; and producing an estimated quantity of the second gas species in the gas stream based on the refined second dataset.

In another embodiment of the present invention, a method for quantifying a target gas species in a gas sample includes: receiving data from a chemical instrumentation system, the data indicating quantities of a plurality of gas species in the gas sample; detecting local mass spectral maxima of the gas sample to calculate initial concentrations of the target gas species; determining concentrations of interfering species, the interfering species having mass to charge ratios (m/z) being similar to an m/z ratio of the target gas species; and adjusting the local mass spectral maxima of the gas sample based on the concentrations of interfering species to produce an enhanced estimation of the target gas species.

In further embodiments, any of the features, functionality and alternatives described in connection with any one or more of FIGS. 1 to 5 may be combined with any of the features, functionality, and alternatives described in connection with any other of FIGS. 1 to 5.

The foregoing brief summary is provided merely for purposes of summarizing some example embodiments described herein. Because the above-described embodiments are merely examples, they should not be construed to narrow the scope of this disclosure in any way. It will be appreciated that the scope of the present disclosure encompasses many potential embodiments in addition to those summarized above, some of which will be described in further detail below.

BRIEF DESCRIPTION OF THE FIGURES

Having described certain example embodiments in general terms above, reference will now be made to the accompanying drawings, which are not necessarily drawn to scale. Some embodiments may include fewer or more components than those shown in the figures.

DETAILED DESCRIPTION

Figure 1:
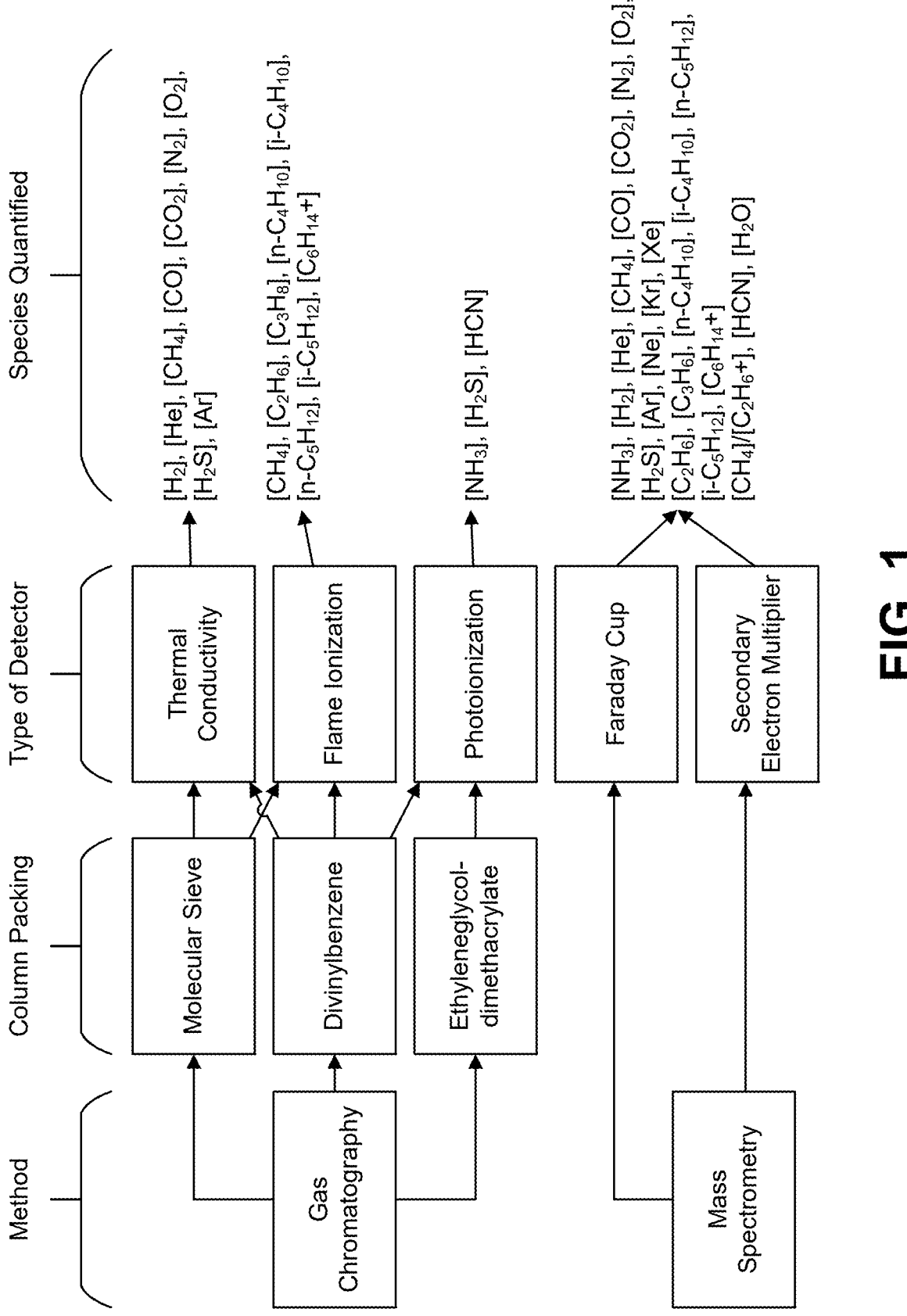
FIG. 1 is a block diagram illustrating an example system for measuring hydrogen ($H_2$), helium (He), ammonia ($NH_3$), hydrocarbon gases (including but not limited to $CH_4$, $C_2H_6$, $C_xH_y$, and other heavier molecular weight hydrocarbons), nitrogen ($N_2$), carbon dioxide ($CO_2$), various hydrogen-derived chemical species (e.g., dihydrogen sulfide ($H_2S$), hydrogen cyanide (HCN)), or other gases in fluids during the drilling of a well or borehole (e.g., mud gas logging). Some embodiments relate to measurements of similar fluids during well or borehole testing (e.g., drill stem testing, formation testing, flow testing, or other production testing) during or after the drilling of a well or borehole, during the monitoring of fluid production from the well or borehole, or the measurement and quantification of the aforementioned chemical species during the gathering, purification, and handling of these compounds, according to an embodiment.

Some example embodiments will now be described more fully hereinafter with reference to the accompanying figures, in which some, but not necessarily all, embodiments are shown. Because inventions described herein may be embodied in many different forms, the invention should not be limited solely to the embodiments set forth herein; rather, these embodiments are provided so that this disclosure will satisfy applicable legal requirements. For instance, features from any of the disclosed embodiments may be used in combination with one another, without limitation. In addition, other features and advantages of the present disclosure will become apparent to those of ordinary skill in the art through consideration of the following detailed description and the accompanying drawings.

As used herein, and unless the context dictates otherwise, the following terms have the meanings as specified below.

The term "geologic hydrogen" generally refers to hydrogen produced from a subsurface geological formation.

The term "geologic hydrogen source" generally refers to hydrogen sourced from any subsurface formations via a wellhead connected to a wellbore or any other pathway from the subsurface to the surface by which geologic hydrogen may be transmitted. Notably, this definition includes hydrogen generated by various mechanisms and chemical mixtures, including hydrogen produced by inorganic (e.g., redox, serpentinization) or radioactive processes. For example, a geologic hydrogen source includes hydrogen produced from a geological formation or accumulations (e.g., at young oceanic crust near a mid-oceanic ridge, continental rift) or other reduced iron deposit (e.g., reduced components of banded iron formation [BIFs]). Geologic formations may include a variety of rock deposits containing complex mixtures or layers of reduced iron mineral phases or organic matter. For example, geologic formations that are suitable for providing a hydrogen feedstock include robust deposits of mafic and ultramafic igneous rock, including olivine- and pyroxene-bearing ores. Rock deposits yield abiotic hydrogen through the reaction of water with the rock deposits to mineralize oxygen and release hydrogen. Other organic-rich rock deposits and fluids can undergo pyrolysis and generate hydrogen during graphitization and/or coalification.

The term "geologic hydrogen derivatives" generally refers to compounds that include hydrogen and are formed in the subsurface or drilling fluid due to natural reactions with geologic hydrogen or reactions resulting from the drilling processes, including reactions with fluids, such as air, or other materials introduced from the drilling or sampling process. Example geologic hydrogen derivatives include ammonia, water vapor, water isotopes, and hydrogen cyanide formed subsurface.

Overview

Embodiments disclosed herein are related to systems and methods for using chemical instruments to rapidly and in real-time detect, measure, and quantify elements or molecules including hydrogen, ammonia, hydrocarbon gases, nitrogen, carbon dioxide, hydrogen-derived chemical species (e.g., dihydrogen sulfide, hydrogen cyanide), or other gases while mud gas logging, testing fluids from the subsurface (e.g., drill stem testing, formation testing, flow testing, or other production testing), or during the gathering, purification, and handling of these compounds at the surface.

The systems and methods for analysis of the bulk combination of chemical species, including hydrogen, hydrogen associated compounds, and non-hydrogen associated compounds (e.g., helium, nitrogen, oxygen, argon, hydrocarbons, carbon dioxide, and water vapor), form the basis of systems and methods used to quantify hydrogen, ammonia, hydrocarbon gases, nitrogen, carbon dioxide, hydrogen-derived chemical species (e.g., dihydrogen sulfide, hydrogen cyanide) within a fluid.

The present specification focuses on systems and methodologies to enable the drilling for, testing of, recovery of, and production of hydrogen, ammonia, hydrocarbons, helium, dihydrogen sulfide, carbon dioxide, or hydrogen derivatives from the subsurface. Other embodiments focus on monitoring, gathering, purification, or handling of these chemical species produced from or synthesized within the subsurface.

It is understood that the techniques disclosed herein are not so limited and find application in the drilling for a variety of naturally occurring molecules, including hydrogen, dihydrogen sulfide, hydrogen derivatives, helium, other noble gases, hydrocarbons, nitrogen, and carbon dioxide. It is also understood that these techniques may include the stimulation and in situ generation or release of hydrogen or other hydrogen derivatives (e.g., enhanced hydrogen production (EHP), enhanced ammonia production (EAP)), the stimulation and in situ generation of hydrogen and simultaneous sequestration of carbon dioxide, dihydrogen sulfide (SEHP), or combinations thereof (SCMEHP), and the production, purification, or handling of those fluids, drilling for the recovery of other natural subsurface resources (e.g., geothermal, minerals/ores, groundwater), and the production, purification, or handling of those resources, drilling for the purpose of subsurface sequestration of fluids (e.g., carbon dioxide, dihydrogen sulfide), gas storage (e.g., hydrocarbons, hydrogen, or helium), brine disposal, enhanced geothermal, and other types of drilling into the subsurface where fluids may be detected, monitored, or quantified.

Gas Profiling at Drilling Operations

Mud logging is the process by which an automated system or an individual, known as a mudlogger, describes the drilled rock and sediment materials, also known as drill cuttings, and analyzes fluids (e.g., drilling mud, mud gas, formation fluids), generally with an instrument such as a gas chromatograph or mass spectrometer, after the fluids are brought to the surface and separated from the circulating drilling fluid (e.g., mud) stream using an agitator or plumbed directly in the case of air drilling. Cuttings, drilling fluids, and formation fluids, including formation gas, are brought to the surface via return of the drilling fluids, or in the case of air drilling the pressurized gas stream during drilling, or in the case of aerated drilling (i.e., drilling underbalanced by injecting air, gases, or other aerosolized fluids) via the drilling fluid that circulates during drilling. In the case of drill stem testing, formation testing, flow testing, or various forms of testing the production of fluids from the subsurface, these fluids are brought to the surface along plumbing from the drill stem.

As these materials are brought to the surface, the mud-logger creates a written log of rock descriptions and a sample catalog of rock materials across the depth of the drilled borehole, a log of fluid volumes and flow rates (e.g., total gas units), and can collect other analytical data (e.g., composition of fluids, including gases released from the formation) throughout various depths of the well or borehole. In some cases, mud logging may include the real-time detection, measurement, and quantification of the gases or other fluids separated from the drilling fluids or, in the case of air drilling the pressurized gas stream during drilling or, in the case of aerated drilling the aerated mud volume, produced during formation testing, drill stem tests, or flow testing, or produced during various other forms of production testing or production activities.

Common gases that can be quantified with varying degrees of analytical certainty described in more detail can include bulk concentrations of hydrocarbons (e.g., methane, ethane, propane, isobutane, normal butane, isopentane, normal pentane, ethene, propene, and larger hydrocarbon compounds), aromatic compounds (e.g., benzene), and other gases (e.g., hydrogen, helium, nitrogen, oxygen, dihydrogen sulfide, argon, carbon dioxide) depending on the suite of instrumentation utilized during the process.

Relevant analytical systems and approaches involved in mud gas logging include gas chromatography and mass spectrometry, which will now be briefly described.

Gas chromatography utilizes the constant flow of a gas called a carrier gas (e.g., helium, hydrogen, nitrogen, or argon) through a column or multiple columns, either nude or packed with various forms of media (e.g., molecular sieve), that are capable of selectively inhibiting the passage of gases through the column and hence allowing for molecular separation of various chemical species. If sufficient inhibition and separation can be achieved, a detector or detectors can be paired with the target chemical species of interest to detect, measure, and quantify various chemical species of interest.

For example, the elements and molecules contained within a given fluid (e.g., gas mixture such as hydrogen, helium, nitrogen, oxygen, methane, carbon dioxide, and heavier hydrocarbons) when injected into the gas stream are separated due to differing efficiencies of transport through the column (e.g., due to molecular volatility and interactions with the column or its media) and are subsequently individually quantifiable using one or another form of a gas chromatography detector (e.g., flame ionization, thermal conductivity).

An alternative approach for mud gas logging analyses that has become more common in the last few decades involves the utilization of near "real-time" mass spectrometry. Gas source mass spectrometers can measure various elements (e.g., helium) and molecules (e.g., hydrogen, methane, carbon dioxide) by eluting a low flow volume of sample gas onto an ion source within a vacuum chamber in a mass spectrometer device. In the mass spectrometer device, the ion source will generate an electron cloud under high vacuum (i.e., low pressures). The ion source will ionize various gas species in the through-passing gas mixture by removing electrons from each atom or molecule and generating elemental or molecular ions. Once ions of various elements (e.g., helium) and molecules (e.g., hydrogen, nitrogen, oxygen, hydrocarbons, carbon dioxide) are formed they can be directed to one or more detectors by a systematically changing magnetic field, separated according to their mass/charge ratio ($m/z$), and detected using Faraday cups, electron multipliers, or various detection systems.

Currently available systems and methods have limited capacity to accurately measure or quantify key components related to hydrogen or helium exploration, and (as described below) are not optimized for more traditional mudlogging purposes including hydrocarbon exploration. Currently available systems and methods are not able to robustly detect and/or quantify hydrogen, key hydrogen derivatives such as ammonia, water vapor, water isotopes, hydrogen cyanide, or others. Similarly, currently available systems and methods are not able to robustly detect and/or quantify helium or other noble gases. Further, these systems can produce inaccurate results for compounds such as nitrogen, carbon dioxide, and other hydrocarbons compared to the anticipated higher analytical precision and accuracy that can be achieved in the laboratory setting. Moreover, in some instances, the currently disclosed analytical methods do not utilize suitable sample preparation systems or methods capable of detecting and measuring these compounds within the analytical precision and accuracy capabilities of commercial chemical instruments.

Some embodiments disclosed herein comprise mud gas logging systems and methods that enable collection, processing, and interpretation of both near real-time detection (qualitative assessment) and quantification of hydrogen, ammonia, and other hydrogen-derived gases (dihydrogen sulfide, hydrogen cyanide).

Hydrogen and other species may be naturally occurring (i.e., geologic), associated with geologic systems related to geologic hydrogen, can be synthesized in the subsurface by injecting key reactants (i.e., enhanced hydrogen production (EHP) or enhanced ammonia production (EAP)), or alternatively may be generated in small quantities by thermal bit metamorphism. Hydrogen generated in varying quantities by any of these processes can be measured in fluids circulated from the borehole to the surface (via the circulation of a well or borehole (e.g., mud gas logging), during well or borehole testing (e.g., drill stem testing, formation testing, flow testing, or other production testing), during or after the drilling of a well or borehole, during the monitoring of fluid production from the well or borehole, or the measurement and quantification of the aforementioned chemical species during the gathering, purification, and handling of these compounds. Hydrogen can be detected, measured, and quantified using the systems and methods included in the embodiments disclosed herein. Hydrogen derivatives, including ammonia, water isotopes, hydrogen cyanide, abiogenic methane circulated to the surface by similar processes flowed from the formation or formed as an artifact of interactions between hydrogen or other chemical compounds within drilling fluids, biocides, mud, water, or air can also be detected, measured, and quantified using the systems and methods included in the embodiments disclosed herein. These chemical species may also relate to feed stock gases or byproducts created during the purification of eluted gases, or during the handling of geologic hydrogen or ammonia during the production of downstream derivative chemicals or products.

Systems and Methods for Enhanced Gas Measurement/Quantification

As illustrated in FIG. 1, example embodiments utilize a device that incorporates a multi-column and multi-detector configuration for simultaneous detection of hydrogen, helium, ammonia, hydrogen cyanide, and other hydrogen derivatives using at least two of the following types of thermal conductivity, flame ionization, and photoionization detection. Some example embodiments utilize multi-column and multi-detector gas chromatography for mud gas logging purposes as described herein. Historically, mud gas logging utilizes gas chromatography with either flame ionization detectors (i.e., primarily for hydrocarbons) or thermal con-ductivity detectors (i.e., for mixtures of hydrocarbons and other gases such as nitrogen). However, traditional gas chromatography configurations fail to utilize other types of detectors, because legacy implementations have not dem-onstrated any apparent need for alternative instrumentation designs.

In contrast, example embodiments disclosed herein include the utilization of a photoionization detector for the detection and quantification of ammonia, hydrogen cyanide, or other hydrogen derivative phases alone or in combination with other detection systems.

In some embodiments, the systems and methods of the present application utilize the photoionization detector alone or in combination with a flame ionization detector, thermal conductivity detector, or other detection system for simul-taneous detection of hydrogen, ammonia, hydrogen cyanide, water vapor, water isotopes, and other hydrogen derivatives, in addition to individual hydrocarbon molecules (e.g., meth-ane, ethane, propane, isobutane, normal butane, isopentane, normal pentane, hexanes) and other gases (e.g., helium, nitrogen, dihydrogen sulfide, oxygen, carbon dioxide).

An embodiment of this invention is the selection of the carrier gas intended for analyses of hydrogen, ammonia, helium, noble gases, and other hydrogen derivatives. Legacy mud gas logging systems have utilized either hydrogen or helium gas as the carrier gas species for fluid detection and quantitative analyses. However, the inventors have deter-mined that, in the context of geologic hydrogen exploration in particular, the use of hydrogen or helium as a carrier gas species obscures the ability of the mud gas logging process to generate accurate analytical results. Accordingly, in some embodiments, the systems and methods of the present appli-cation utilize argon gas to maximize the sensitivity and specificity for hydrogen, helium, ammonia, hydrogen cya-nide, or other species by mud gas logging detection and quantification.

Another embodiment of this invention is the utilization of an ethylene glycol-dimethacrylate packed gas chromatogra-phy column for separation of ammonia or other hydrogen derivatives from water (FIG. 1). Historically, mud gas logging implementations have utilized one or combinations of molecular sieve packed and/or divinylbenzene packed gas chromatography columns for the separation of individual hydrocarbon molecules (e.g., methane, ethane, propane, isobutane, normal butane, isopentane, normal pentane, hexanes) and other gases (e.g., nitrogen, dihydrogen sulfide, oxygen, argon, carbon dioxide).

In contrast, the systems and methods of the present application utilize an ethylene glycol-dimethacrylate packed gas chromatography column in combination with molecular sieve packed and/or divinylbenzene packed gas chromatog-raphy columns for simultaneous detection of hydrogen, ammonia, hydrogen cyanide, water vapor, water isotopes, and other hydrogen derivatives, in addition to individual hydrocarbon molecules (e.g., methane, ethane, propane, isobutane, normal butane, isopentane, normal pentane, hexanes) and other gases (e.g., helium, nitrogen, dihydrogen sulfide, oxygen, argon, carbon dioxide).

The ethylene glycol-dimethacrylate packed gas chroma-tography column enables robust detection and analysis of ammonia, hydrogen cyanide, water, water isotopes, and other hydrogen derivatives components by adequately pro-viding baseline separation of water vapor relative to these other phases (e.g., ammonia, methane). Water vapor can be a significant component of formation fluids sampled during mudlogging, well or borehole testing (e.g., drill stem testing, formation testing, flow testing, or other production testing), during the monitoring of fluid production from the well or borehole, or the measurement and quantification of the aforementioned chemical species during the gathering, puri-fication, and handling of these compounds. However, water vapor specifically interferes with the detection and quanti-fication of ammonia and/or methane (in both gas chroma-tography and mass spectrometry)

It is noted that utilization of an ethylene glycol-dimeth-acrylate packed gas chromatography column used in com-bination with molecular sieve packed and/or divinylbenzene packed gas chromatography columns can be carried out as separate columns that require splitting a gas stream in order to allow gas to flow to different detection systems, or as one or more series of columns leading to a single detector. For example, a gas stream flowed first through a divinylbenzene packed gas chromatography column and subsequently into an ethylene glycol-dimethacrylate packed gas chromatogra-phy column in order to more completely separate out different chemical species and elute different target gases onto the detector at controllable times. It is also conceived that separation can be achieved through a combination of column plumbing systems and detectors.

Legacy mud gas logging analyses described above use gas source mass spectrometers (e.g., quadrupole residual gas analyzer mass spectrometers) to quantify gas concentrations of elements and molecules within a chosen mass to charge range (e.g., m/z approximately 1-300). Thus, these systems can detect and quantify various gases, including select low molecular weight hydrocarbons (e.g., methane, ethane, pro-pane, isobutane, normal butane, isopentane, normal pen-tane), higher molecular weight hydrocarbon compounds, organic compounds (e.g., benzene), and other gases (e.g., hydrogen, helium, nitrogen, oxygen, dihydrogen sulfide, argon, carbon dioxide) with varying degrees of analytical accuracy and precision pertaining to method detection lim-its, signal to noise ratios, mass spectral interferences, and spectral overlaps. The utility of commercially available systems is limited by one or more factors.

While the ionization of an individual chemical species in a given gas source mass spectrometer is consistent over time with respect to analytical tolerances (±10%), ionization is neither 100% efficient, nor can it be assumed to be uniform when measuring various mixtures of fluids. Ionization effi-ciency is below 100% because the ionization energies differ between different elements and molecules, and there can be shielding between the electron beam formed by the filament target elements or molecules, which would inhibit the for-mation of ions in the gas cloud within the mass spectrometer vacuum chamber.

In addition to the observed differences in ionization efficiency related to the removal of the first electron from various elements and molecules, these elements and compounds are also susceptible to further ionization (i.e., removal) of secondary, tertiary, or other additional electrons. Removing additional electrons may result in fractals superimposed on other m/z ranges that produce additional mass spectral interferences. For example, if two electrons were removed from argon-40 during ionization, the resulting doubly charged ion would create a m/z=20 instead of the m/z=40 that would be expected for 40Ar+. It is only if this specific proportion of ions is accounted for that the true value of a species with a m/z=20 can be quantified. Similarly, the uncertainty in the quantification of argon-40 increases if the proportion of 40Ar(2+) is large and/or poorly constrained. The variable ionization behavior of individual gas species within a gas mixture that is injected into a gas source mass spectrometer can lead to signal overlaps (i.e., "spectral" or "superposition" overlaps) and make it difficult or impossible to quantify certain gas species if they are obfuscated by other gas species.

The presence of multiple chemical species with similar mass ranges (e.g., ammonia, water vapor, and methane) can similarly result in mass spectral interference challenges and also make it difficult or impossible to quantify certain gas species. For example, when ammonia is ionized in quadrupole residual gas analyzer mass spectrometers, approximately 0.26% of the total ammonia atoms is expected to be measured at m/z=18, approximately 52.49% is expected to be measured at m/z=17, approximately 41.99% is expected to be measured at m/z=16, and approximately 4.20% is expected to be measured at m/z=15. By comparison, when methane is ionized, approximately 0.55% of the total methane molecules is expected to be measured at m/z=17, approximately 45.93% is expected to be measured at m/z=16, and approximately 39.50% is expected to be measured at m/z=15. Additional complexity occurs when water vapor, which is typically an incidental contaminant, is present in the gas mixture and is ionized, approximately 74.40% of the total water molecules is expected to be measured at m/z=18, approximately 17.11% is expected to be measured at m/z=17, and approximately 8.18% is expected to be measured at m/z=16. Therefore, without adequate sample preparation systems, quadrupole mass spectrometers cannot readily distinguish between certain gases (e.g., ammonia, methane, water vapor) if significant amounts of each are present, the quantities of each compound in the gas mixture are unknown, or additional mass spectral interferences obfuscate quantification of these components. The embodiments described herein disclose sample preparation systems and methods that address these limitations.

In particular, example embodiments utilize quadrupole residual gas analyzer mass spectrometry for the detection and quantification of hydrogen, helium, ammonia, and other hydrogen derivatives, but do so after mitigating the likelihood of spectral interferences noted above.

As one approach, example embodiments utilize condensation/cryogenic separation, which can be accomplished using a combination of chemical traps, chambers, or other devices that are cooled to (or heated to) or held at sufficient temperature to achieve separation of a desired gas species from a remaining gas stream through, for example, evaporation, condensation, or freezing.

An embodiment disclosed in this invention related to the condensation/cryogenic separation of various gas phases involves exposing a gas mixture to sufficiently low temperatures, using either a nude trap (i.e., empty metal vacuum container), a series of nude traps, a vacuum chamber filled with various high surface area sorbent materials (e.g., charcoal, carbon black, zeolites, or other molecular sieve compounds), or a series of vacuum chambers filled with various high surface area sorbent material to separate individual or multiple gas species within a gas mixture based on their mass, chemical behavior, solubility, or known phase states at differing temperature and pressure regimes (e.g., gas, liquid, solid, supercritical).

An embodiment of this invention involves the device and methods for condensation or cryogenic (herein termed condensation/cryogenic for simplicity as opposed to considering each individual temperature ranges for the condensation or freezing of each element or molecule) separation of liquid- and gas-phase water from other gases and condensation/cryogenic separation of various gas components prior to introduction into a gas mass spectrometer system. The utilization of the condensation/cryogenic separation or distillation device and process enables near real-time and continuous detection and quantification of hydrogen, ammonia, and other hydrogen-derived chemical species (e.g., hydrogen cyanide) by creating condensation/cryogenic separation of gas species that would otherwise have mass spectral interferences either directly or as a fractal produced during ionization, including water vapor, methane, other hydrocarbons, and carbon dioxide among others. Another embodiment of this invention is that following the removal of the aforementioned gas species, the method detection limit, analytical precision, and accuracy of detecting, measuring, and quantifying hydrogen, ammonia, and other hydrogen derivative measurements are improved relative to bulk gas measurements.

Historical approaches for mud gas logging described above do not use condensation/cryogenic separation as a method of separating water from gas, nor as a method of condensation/cryogenic separation of non-water gases to optimize the detection and quantification of hydrogen, ammonia, or other hydrogen-derived chemical species (e.g., hydrogen cyanide), in addition to hydrocarbons and other gases (e.g., helium, nitrogen, dihydrogen sulfide, oxygen, argon, and carbon dioxide).

Moreover, certain example embodiments further include the utilization of externally powered devices to maintain or modulate temperatures for the purposes of condensation/cryogenic separation for mud gas logging analyses. This embodiment can include the use of cold fluid baths, chilled fluid bath circulation systems, recirculating chillers, condensation/cryogenic pumps, condensation/cryogenic traps, tunable cold heads or cold traps, or other devices used to maintain or modulate temperatures of a vacuum, traps, or sample preparation line.

An embodiment of this invention includes the utilization of liquid nitrogen maintained as a pure liquid at liquid nitrogen temperatures (−196° C.) for the purposes of condensation/cryogenic separation for mud gas logging as described above. Another embodiment includes the utilization of liquid nitrogen as a component in a mixture with another fluid or fluids as a method of maintaining or modulating temperatures to greater than liquid nitrogen temperatures (−196° C.), but below the freezing temperatures of water (0° C. at 1 atmosphere) for the purposes of condensation/cryogenic separation for mud gas logging as described above. This embodiment can include mixing liquid nitrogen with a fluid or fluids that have lower freezing temperatures than water including ethanol, methanol, acetone, and other compounds, to produce a temperature range between $-190°$ C. and $-10°$ C. in order to achieve molecule specific separation.

One embodiment of this invention further improves the method detection limit, analytical precision and accuracy of detection, measurement, and quantification of helium, argon, and other noble gas resources (e.g., neon, krypton, xenon). This embodiment can include condensation/cryogenic separation that produces baseline separation of noble gas species from water vapor, ammonia, carbon dioxide, hydrocarbons, and other gases more commonly analyzed using mass spectrometric based mud gas logging.

In one embodiment, chemical separation of noble gases is achieved using chemical getters to remove reactive gases (e.g., hydrogen, carbon dioxide, nitrogen, hydrocarbons, ammonia); the removal of the reactive gases achieves further baseline separation of noble gases. Further separation of various noble gas species can be achieved using condensation/cryogenic separation in nude vacuum chambers or vacuum chambers filled with various sorbent materials described earlier. In other embodiments, condensation/cryogenic separation chambers (i.e., using nude vacuum chambers or vacuum chambers filled with sorbent materials) can be paired with a chemical getter (a reactive material placed inside a vacuum chamber to chemically react with and remove active gases).

Because legacy mud gas logging implementations do not utilize condensation/cryogenic separation, either using nude or sorbent traps, as described in this embodiment, such implementations cannot with any ordinary analytical certainty (precision or accuracy of less than 50% error) detect or quantify ammonia, other hydrogen-derived chemical species (e.g., hydrogen cyanide) or improve the specificity and/or detection/quantification of noble gases.

Another embodiment of the current disclosure relates to improved measurement of hydrogen, methane, water vapor, or nitrogen. The mass spectral range from m/z=14 to m/z=19, as documented above, contains a series of difficult to resolve interferences with gases of interest in mud gas logging or in other mud gas measurement while drilling practices. Interfering chemical species of interest include, water vapor, ammonia, methane, as well as doubly ionized (i.e., "doubly charged") species of ethane or nitrogen, and triply ionized (i.e., "triply charged") species of carbon dioxide or propane. As a result, the use of condensation/cryogenic separation or chemical gettering (i.e., removal) described above not only improves the detection and quantification of noble gases, but additionally allows for sequential removal of various mass spectral interferences and quantitatively improves the accuracy and precision of water vapor detection and quantification, methane detection and quantification, ammonia detection and quantification, nitrogen detection and quantification, among others.

One embodiment of the current disclosure is the improvement in the detection and quantification of each of these species. This embodiment is achieved in two ways. Firstly, chemical removal aids in the specification of individual chemical species by the removal of spectral interferences. Secondly, if the mass spectral interference can be reduced to relatively small quantities, the mass spectrometer operating conditions can be tuned to minimize mass spectral (or superposition) interferences, enabling the deployment of software-based approaches that calculate the signal intensity of various interferences and correct the signal at a given mass/charge ratio of interest. As long as the interference can be sufficiently reduced to a relatively small proportion of the total signal (e.g., less than approximately 50%), such solutions can be used to confirm detection of various chemical species more accurately and quantify their abundance. An embodiment of this disclosure is the deployment of computer-driven solutions to quantify mass spectral interferences and correct measured signals to enable establishment of robust method detection limits and improve the quantification of various aforementioned chemical species.

After a mass spectrometer analysis is complete, the results are output to a raw data file (e.g., ASCII or CSV format). Computer programmed routines can read the raw data and process the outputs to produce corrected results. Routine tasks can include identifying peak values by detecting local mass spectral maxima to select appropriate chemical standards for calibration (e.g., determine whether the concentration of $H_2$ exceeds standardized values (e.g., >10%) to apply a matrix dependent and quantitatively determined correction to the measured concentration). Additionally, known interferences at specific m/z values can be accounted for by determining concentrations of interfering species from concurrent analyses from other instrument outputs (e.g., from another mass spectrometer or gas chromatograph) and the proportions of these species can be removed from the signals to determine contribution from various mass spectral interferences at a given m/z value in order to correct the measured concentration. These routines can run in near real-time by detecting when outputs are produced and comparing the timestamps in runs to relate measurements taken from separate instrument scans.

The ability to detect, quantify, and separate key chemical species, including ammonia, water vapor, methane, ethane, nitrogen, and propane, is also critical to more robust detection and quantification of hydrogen (and other hydrogen-derived species). Spectral interferences in m/z=1, 2, and 3 are observed in the presence of hydrocarbon, water vapor, or ammonia stemming from various hydrogen fractals generated during the ionization of these compounds or recombined following fragmentation (e.g., cleaving off) of hydrogen during ionization. Thus, if unresolved or unquantified, these chemical species can also interfere with the quantification of hydrogen due to ionization fractals that are fragmented off or cleaved off (i.e., derived from) during the ionization of hydrogen-containing chemical species that lead to mass spectral interferences with measuring hydrogen (or other compounds). An embodiment of the current disclosure is the improved detection and quantification of hydrogen that can be achieved through the condensation/cryogenic separation of other chemical species containing hydrogen in the parent molecules prior to ionization. Specific examples include potential interferences from ammonia, water vapor, methane, and other hydrocarbon gases, whose removal quantitatively reduces the background for hydrogen and improves detection and quantification of hydrogen measurements. An embodiment of this disclosure is the deployment of computer-driven solutions for quantifying mass spectral interferences and correcting measured signals, which improve the quantification of hydrogen. An embodiment of this disclosure is the establishment of lower, spectral interference corrected analytical baselines (i.e., lower signal-to-noise ratios), more robust and lower limits of detection (LOD), limits of quantification (LOQ), and method detection limits (MDLs), which improve the quantification of hydrogen.

Figure 2:
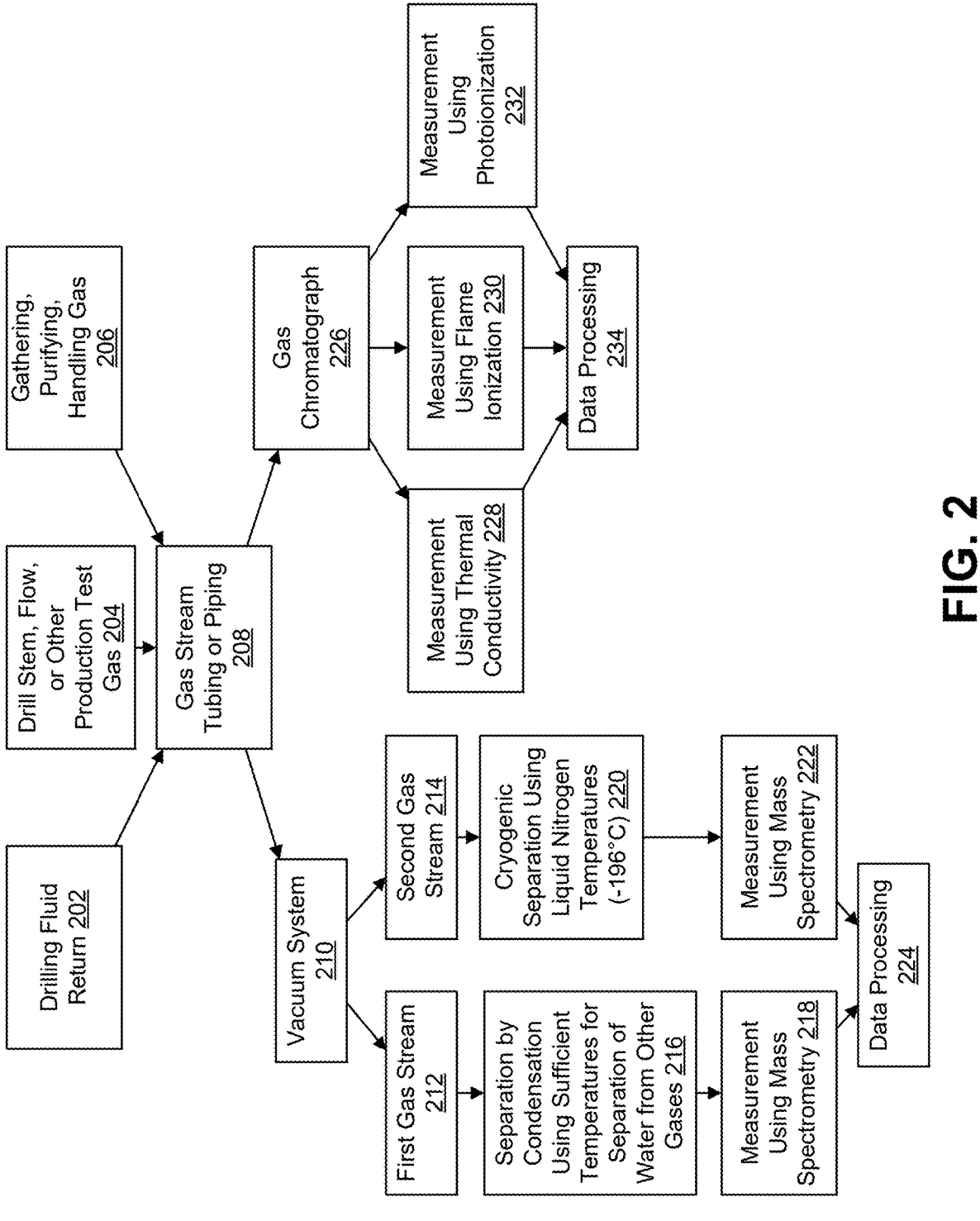
FIG. 2 is a flow chart illustrating an example method for the detection and quantification of hydrogen, helium, ammonia, hydrocarbon gases, nitrogen, carbon dioxide, various hydrogen-derived chemical species (e.g., dihydrogen sulfide, hydrogen cyanide), or other gases in fluids during the drilling of a well or borehole (e.g., mud gas logging). Some embodiments relate to measurements of similar fluids during well or borehole testing (e.g., drill stem testing, formation testing, flow testing, or other production testing) during or after the drilling of a well or borehole, during the monitoring of fluid production from the well or borehole, or the measurement and quantification of the aforementioned chemical species during the gathering, purification, and handling of these compounds, according to an embodiment.

Individually or together, condensation/cryogenic or a combination of condensation/cryogenic and gettering processes can preclude or remove mass spectral interferences (i.e., signal overlap or superposition interferences) and allow rapid, continuous, and high-fidelity measurement of hydrogen, ammonia, methane, nitrogen, helium, other noble gases, and other gases. As shown in FIG. 2 an embodiment of this invention includes a device for real-time and simultaneous detection and quantification of hydrogen, ammonia, and other hydrogen-derived chemical species (e.g., hydrogen cyanide), in addition to hydrocarbons (methane, ethane, propane, isobutane, normal butane, isopentane, normal pentane, hexanes) and other gases (e.g., helium, nitrogen, dihydrogen sulfide, oxygen, argon, and carbon dioxide) through the utilization of condensation/cryogenic separation and mass spectrometry. This embodiment includes a single gas stream 208 (which may be received from drilling fluid (e.g., drilling mud) return 202, drill stem, flow, or other production test gas 204, or gathering, purifying, or handling gas 206) that can be split into two or more equivalent gas streams. One gas stream may continue to a gas chromatography configuration 226, which may perform measurement using thermal conductivity 228, flame ionization 230, or photoionization 232, followed by data processing 234 to produce an analytic result. The other gas stream may be exposed to a condensation/cryogenic chamber, or in some cases chemical getters, for the purposes of condensation/cryogenic or chemical separation prior to instrument measurement.

In this embodiment, the gas streams 212, 214 may pass through chambers filled with sorbent material (e.g., desiccant, sorbent, or getter) as a method to separate water vapor from other gases or separate non-water gas species before or after condensation/cryogenic separation, or as a replacement for condensation/cryogenic separation. This sorbent material may be externally cooled or heated, held at ambient temperatures, or subjected to modulating temperatures to achieve specific gas species separations. In this embodiment, the gas streams can be injected into a high vacuum system 210 prior to or after condensation/cryogenic or chemical separation 216, 220 prior to instrument measurement 218, 222 and subsequent data processing 224.

Figure 3:
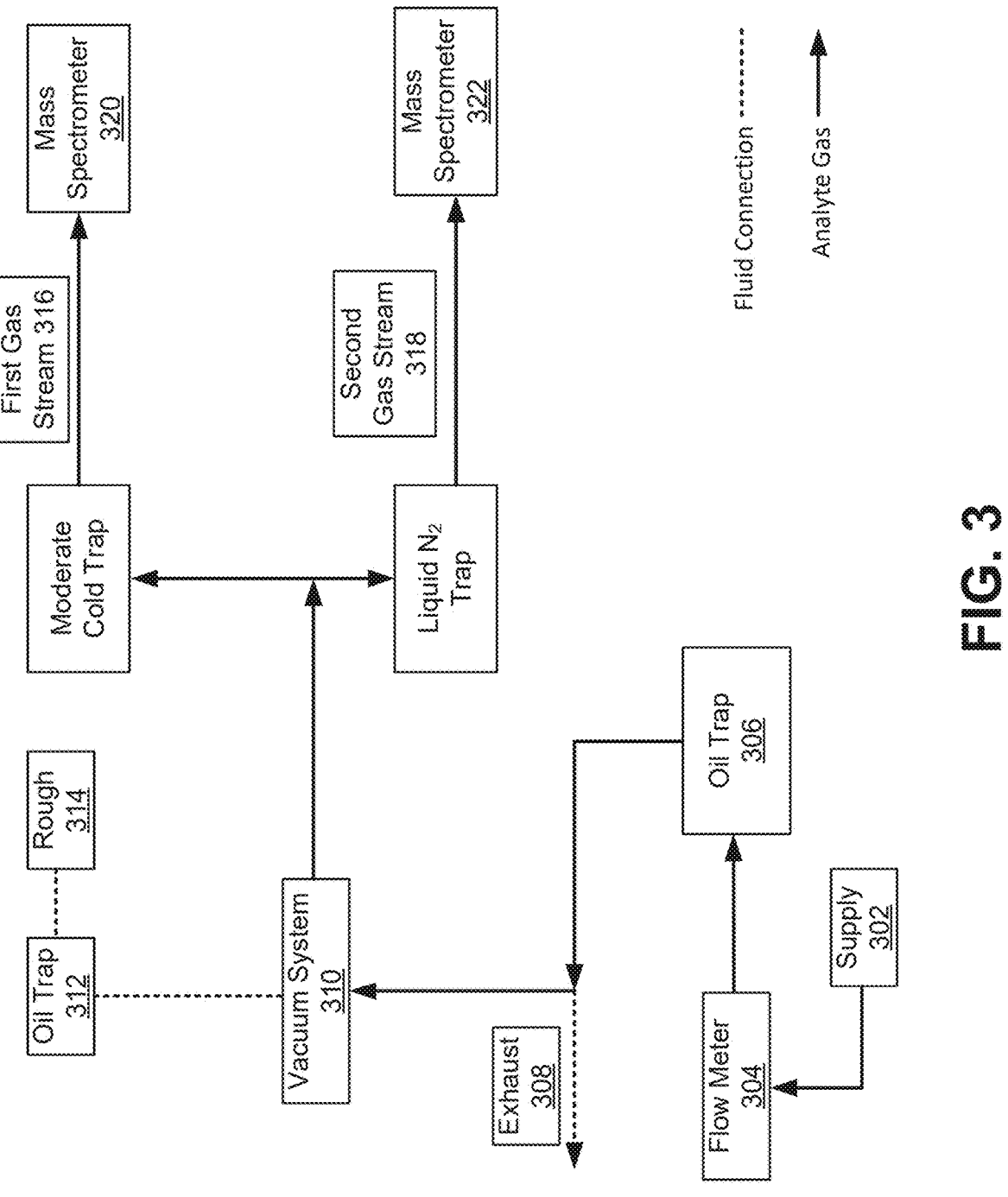
FIG. 3 is a diagram of an example system for the rapid and near real-time detection, measurement, and quantification of elements or molecules including hydrogen, helium, ammonia, hydrocarbon gases, nitrogen, carbon dioxide, hydrogen-derived chemical species (e.g., dihydrogen sulfide, hydrogen cyanide), or other gases during drilling, testing, production, gathering, purification, and handling of the aforementioned chemical compounds.

As shown in FIG. 3, some stages of chemical separation can be achieved at standard/working pressures and temperatures. For instance, a supply 302 of gas may be received at a flow meter 304, which introduces a metered volume of gas into a mass spectrometry configuration. In some embodiments, an oil trap 306 may capture liquids (e.g., liquid hydrocarbons), after which certain constituents of the remaining gas are removed from the system via exhaust 308 (e.g., a vent or vacuum pump), while a remaining gas stream continues into vacuum system 310. Following further removal of impurities via oil trap 312 or rough pump 314, the gas may be separated into two additional gas streams 316, 318, held at varying temperatures to prompt separation of still further constituent components as described herein. Having removed many of the constituent gas species in each of these gas streams 316 and 318, mass spectrometers 320 and 322 may be used to measure and/or quantify the remaining gas species with enhanced accuracy.

In an example embodiment, following the splitting of a single gas stream for the purposes of chemical analyses using one or more of gas chromatography, mass spectrometry, and/or other instrumentations, those gas streams may be further split for the purposes of chemical separation and/or condensation/cryogenic separation, and/or other methods for the purposes of improving detection (LOD) and quantification (e.g., LOQ or MDL) of gases prior to their introduction into chemical instrumentation. An example embodiment involves a single gas stream going to a mass spectrometry system that is split into two identical gas streams: a first and second gas stream. For this example, it is noted that while the first and second gas streams for mass spectrometry are labeled hereafter as "first MS gas stream" and "second MS gas stream", these labels are for identification purposes only and do not necessarily imply a chronological order of operation or difference of importance.

In this embodiment, the condensation/cryogenic chamber for the first MS gas stream 316 is held at sufficient temperatures to adequately condense or cryogenically freeze water vapor onto nude chemical traps or chemical traps impregnated with a sorbent material (e.g., charcoal, molecular sieve), while not condensing or freezing hydrogen, ammonia, or other hydrogen-derived chemical species (e.g., hydrogen cyanide), in addition to hydrocarbons (methane, ethane, propane, isobutane, normal butane, isopentane, normal pentane, hexanes) and other gases (e.g., helium, nitrogen, dihydrogen sulfide, oxygen, argon, and carbon dioxide). The removal of water vapor is critical toward the removal of mass spectral interferences with ammonia and/or methane. In this embodiment, this temperature can range from approximately −78° C. (freezing point of carbon dioxide at 1 atmosphere pressure) to 0° C., while the condensation/cryogenic chamber for the second MS gas stream is held at liquid nitrogen temperatures (−196° C.). After the condensation/cryogenic chambers, the two gas streams are injected into separate mass spectrometer instruments.

In an embodiment, the mass spectrometer 320 for the first MS gas stream will be able to detect and quantify hydrocarbons (e.g., methane, ethane, propane, isobutane, normal butane, isopentane, normal pentane, and larger hydrocarbon compounds), organic compounds (e.g., benzene), and other gases (e.g., hydrogen, helium, nitrogen, oxygen, dihydrogen sulfide, argon, carbon dioxide). Where gas species overlap based on the ionization behavior in the mass spectrometer (such as the overlap between methane and ammonia at m/z=15, 16, 17, or 18), the resulting measurement at the m/z unit where overlap occurs represents the sum of all of the different species' proportions of total signal intensity at that m/z unit. For example, in a gas mixture where methane and ammonia are present, the 41.99% of the total ammonia molecules are expected to be measured at m/z=16 add to the 45.93% of the total methane molecules expected to be measured at m/z=16.

In this embodiment, the second MS gas stream 318 would flow through a condensation/cryogenic chamber held at liquid nitrogen temperatures (−196° C.) or tuned to achieve temperatures from −265° C. to 25° C. or even heated to higher temperatures, which will lead to condensation/cryogenic separation of water, carbon dioxide, and other gas species from the gas stream. At liquid nitrogen temperatures, gases including helium, hydrogen, methane, nitrogen, argon, other noble gases, and other targeted gases can remain in the gas phase and may be detected and quantified, notably with improved analytical accuracy and precision during the measurement of each of these compounds by gas mass spectrometer 322. In contrast, ethane and heavier hydrocarbons, other organic compounds (e.g., benzene), carbon dioxide, dihydrogen sulfide, oxygen, ammonia, and other non-targeted gases can be condensed or frozen out of the gas stream and are thus not detectable or quantifiable by gas source mass spectrometry.

An embodiment of this invention includes the automatic correction and reconciliation of data from one or more instruments for the purpose of improving gas measurement and automated data processing. Following the raw measurement of a gas mixture using one or more mass spectrometers and/or one or more gas chromatographs, the data is generally exported as, for example, one or more tabular or ASCII data files. For mass spectrometers, exported raw data may be in the form of an amperage across a m/z range, or as partial pressures across a m/z range such as in the case of quadrupole residual gas analyzer mass spectrometers. Software for gas chromatography can often output raw abundances (i.e., areas under the curve as determined by various detection methods) automatically (e.g., as volume percent, as a percentage or area under a curve) by quantifying the areas of a gas species as a function of voltage or amperage multiplied by time (i.e., integrating area under the peak curve), but these raw data are relative and uncalibrated to chemical standards.

An embodiment of this invention uses chemical standards (e.g., gas calibration standards) to quantitatively determine the proportion of interference observed at a superimposed mass/charge ratio and automatically deploy an adjustment, based on the proportion of interference, to correct the signal at the intended mass/charge ratio. In this embodiment, chemical standards are analyzed in equivalent manners as the unknown gas mixtures. The measured relative signal intensity of gas species of the chemical standard mixtures by the instrument are then divided by the reported absolute abundances of the chemical standard to generate a calibration curve for the concentration of a given analyte and to determine the signal correction factors for that analyte by measuring the signal intensity at the m/z of various spectral interferences, which can then be applied to unknown gas mixtures. The signal correction factors are used to adjust raw data based on variable measurement efficiency of individual gas species in an instrument (e.g., at relevant m/z units in a mass spectrometer), which may change over time (e.g., over the life span of a mass spectrometer source filament), and to convert the raw data from relative data of non-standardized units (e.g., based on the type of instrument) to absolute abundances of mole or volume percent.

For example, the peak area signal for an argon peak at m/z=40 measured on a standard gas of known concentrations (e.g., 3,000 counts per second per part per million of argon or $2 \times 10^{-9}$ torr per part per million of argon) can be used to calibrate the signal response (e.g., amps/torr of argon) of a known gas standard for a given instrument; this approach integrates a standard response that includes, among other analytical factors, ionization efficiency, detector sensitivity, detector gain, etc.). In this embodiment, the exported files from each instrument can be automatically processed to first determine analytical sensitivity of a given analyte-instrument pair, next to determine presence of and quantify the abundance of the generation of mass spectral interferences generated by that known compound, and finally to calculate the contributions of a mass spectral interference on at the m/z of other compounds. Implementations including this technique enable signal corrections based on measuring a given instrument's response to known concentrations of one or more compounds, the ionization efficiency, and the contributions to mass spectral interferences. Using this approach, the raw data can be reconciled by combining the results from the one or more instruments and/or detectors to correct for mass spectral interferences from one or more compounds, and ultimately improve detection limits and quantification of gas species in a gas mixture, as well as generate a fully processed composition (e.g., as mole or volume percent) of a gas mixture.

In this embodiment, computer programming routines can be automatically applied to the raw tabular data to analyze and subsequently choose appropriate chemical standards based on apparent raw abundances of specific gas species (e.g., hydrogen or ammonia at parts per million levels or >10%) or detector type (e.g., an ammonia standard when using the photoionization detector or a hydrocarbon standard when using a flame ionization detector). The software code driving these routines can be written in a scripting programming language (e.g., Python, Bash, Perl, etc.), or using other coding techniques as may be required.

In an embodiment, once signal correction factors are determined through the use of chemical standards, computer programming routines may then automatically reconcile and relate data between one or more mass spectrometers and/or gas chromatographs with one or more detectors and/or other chemical instruments utilized for the purposes of quantifying gases within a gas mixture, and may quantify and remove mass spectral interferences or overlaps, and calculate gas abundances with improved accuracy.

The mass spectrometer 320 for the first MS gas stream 316, which is passed through a condensation/cryogenic chamber that is chilled to sufficiently cold temperatures to remove water from the vapor phase (i.e., condense or freeze the water vapor) or other chemical species, will be able to detect and quantify hydrocarbons (e.g., methane, ethane, propane, isobutane, normal butane, isopentane, normal pentane, and larger hydrocarbon compounds), organic compounds (e.g., benzene), and other gases (e.g., hydrogen, helium, nitrogen, oxygen, dihydrogen sulfide, argon, carbon dioxide), but these measurements may also include the proportions of overlapping gas species. The mass spectrometer 322 for the second MS gas stream 318, which passed through the condensation/cryogenic chamber held at liquid nitrogen temperatures ($-196°$ C.) or tuned to achieve temperatures from $-265°$ C. to $+100°$ C., will be able to detect and quantify hydrogen at m/z=2, helium at m/z=4, methane at m/z=15 or 16, nitrogen at m/z=28, and argon at m/z=40 due to the removal of overlapping gas species.

In this example embodiment, the measurements of hydrogen, helium, methane, nitrogen, and argon from the second MS gas stream can be performed with improved precision and accuracy, but are relative to the proportion of gas remaining following prior episodes of condensation/cryogenic separation, chemical gettering, etc. This stems from the fact that these measurements do not include other gases that may represent significant portions of the original gas mixture (e.g., carbon dioxide, heavier hydrocarbons) that were previously condensed and/or which may have produced mass spectral interferences that could have obfuscated or overlapped with the mass range of the analyte(s) of interest.

Figure 4:
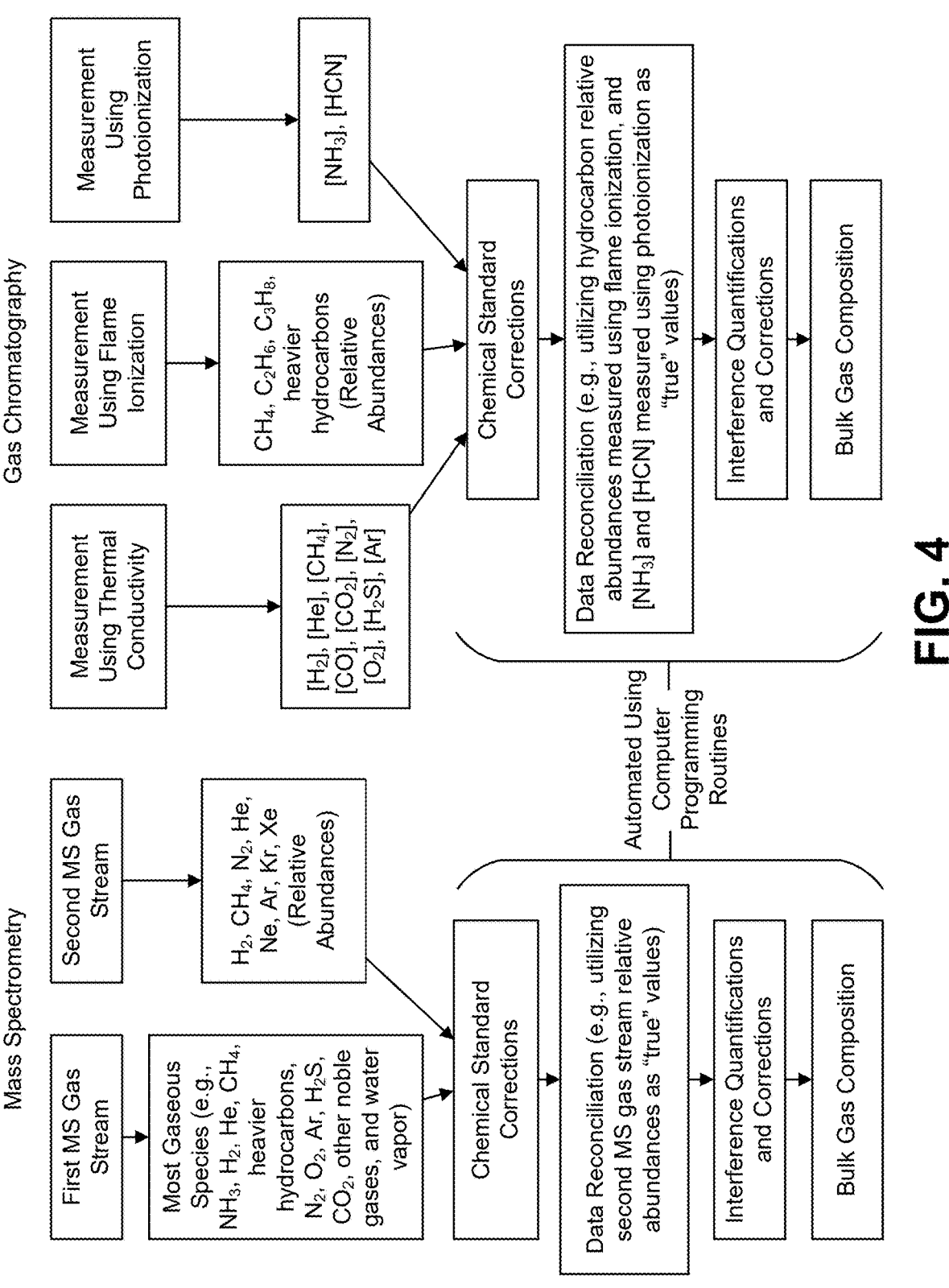
FIG. 4 is a flow chart illustrating an example method for the detection, quantification of, and data processing pertaining to hydrogen, helium, ammonia, hydrocarbon gases, nitrogen, carbon dioxide, various hydrogen-derived chemical species (e.g., dihydrogen sulfide, hydrogen cyanide), or other gases in fluids during the drilling of a well or borehole (e.g., mud gas logging). Some embodiments relate to measurements of similar fluids during well or borehole testing (e.g., drill stem testing, formation testing, flow testing, or other production testing) during or after the drilling of a well or borehole, during the monitoring of fluid production from the well or borehole, or the measurement of the aforementioned chemical species during the gathering, purification, and handling of these compounds, according to an embodiment.

The relative abundances measured in the second MS gas stream may thus represent more accurate and precise measurements of target compounds that can be applied to measurements made in the first MS gas stream using computer programming routines with careful instrument calibration and matrix matched standards. In this embodiment, reconciling the data from the two mass spectrometers may include utilizing gas species measured on both mass spectrometers that have minimal or no potential interferences from overlapping compounds, such as hydrogen (m/z=2, 3) and helium (m/z=3, but dominantly 4) (FIG. 4).

The ratios between gas species measured in the second MS gas stream, for example to hydrogen or helium (i.e., $H_2/He$, $H_2/CH_4$, $H_2/N_2$, $H_2/Ar$ or $He/CH_4$, $He/N_2$, $He/Ar$), represent reliable ratios that may be automatically applied using computer programming routines to the measurements made by the mass spectrometer 320 for the first MS gas stream 316, which will be used to calculate the bulk gas composition. For example, the abundance of helium may be measured with relatively high precision and accuracy on the mass spectrometer of the first MS gas stream due to the general lack of mass spectral interferences at m/z=4, and the reliable He/CH$_4$ ratio measured in the second MS gas stream can then be used to calculate a more accurate methane abundance in the first gas stream's gas mixture.

In this embodiment, another method of reconciling data involves using the second MS gas stream's measured signals from the mass spectrometer relative to an external parameter such as pressure of the gas mixture (e.g., amps/torr) in the mass spectrometry and/or vacuum system (e.g., prior to and after condensation/cryogenic separation and/or chemical getter), which can be used to calculate an abundance of targeted gas species in the gas mixture if compared to the signal/pressure measurement of the same gas species in a chemical standard. Once calculated, the abundances of gases in the second MS gas stream (e.g., H$_2$, He, N$_2$, O$_2$, Ar) can be reconciled with the bulk gas composition measured using the first MS gas stream.

It is noted that depending on the composition of the gas mixture, other compounds measured in the second MS gas stream, which passed through the condensation/cryogenic chamber, either as a nude trap or with chemical sorbents held at liquid nitrogen temperatures (−196° C.) or tuned to achieve temperatures from −265° C. to +100° C., such as nitrogen or argon, could also be used to reconcile data or validate data processing algorithms from the two or more mass spectrometers during data processing. Thus, data reconciliation between two gas streams split from a single gas mixture can be used to improve the detection limits and calculate more accurate abundances of hydrogen, nitrogen, argon, ammonia, and other gases (e.g., noble gases) in a gas mixture if sufficient gas chemical separation is achieved between the targeted gas species and any mass spectral interferences, overlaps, or potential fractals formed during the ionization of other compounds in a mass spectrometer through the utilization of chemical sorbents and/or temperature modulation meant to achieve condensation/cryogenic separation as described above. Data reconciliation in the manners described above can also be automatically conducted using computer programming routines that compile and process the data from different sources (e.g., mass spectrometers and/or gas chromatographs) as soon as the coupled analyses are complete and allow for the calculation of bulk gas composition in near real-time.

In this embodiment, computer programming routines can be used to reconcile data generated through one or more gas chromatography detectors from one or more instruments, and/or reconcile gas chromatography data with data generated through mass spectrometry or other chemical instrumentation with the purposes of analyzing gases within a gas mixture. In an example embodiment, a flame ionization detector may quantify with high accuracy and precision the relative abundances of hydrocarbons (e.g., CH$_4$/C$_2$H$_6$, CH$_4$/C$_2$H$_6$, CH$_4$/C$_x$H$_y$, etc.), the thermal conductivity detector may quantify hydrogen, helium, methane, nitrogen, oxygen, hydrogen sulfide, carbon dioxide, and other compounds, and the photoionization detector may quantify ammonia. In this example, the relative hydrocarbon abundances measured by the flame ionization detector can be automatically extracted by computer programming routines and put into the context of the bulk gas mixture using the methane abundance generated by the thermal conductivity detector to generate absolute abundances of the heavier hydrocarbons. Further, ammonia and other compounds measured using the photoionization detector may automatically be put into context of the bulk gas mixture using computer programming routines that then recalculate the bulk composition after taking into account the additional compounds. These methods can also be applied to multiple instruments and/or different types of instruments (e.g., mass spectrometer and gas chromatography) that are ultimately measuring gas species within a single gas mixture.

Figure 5:
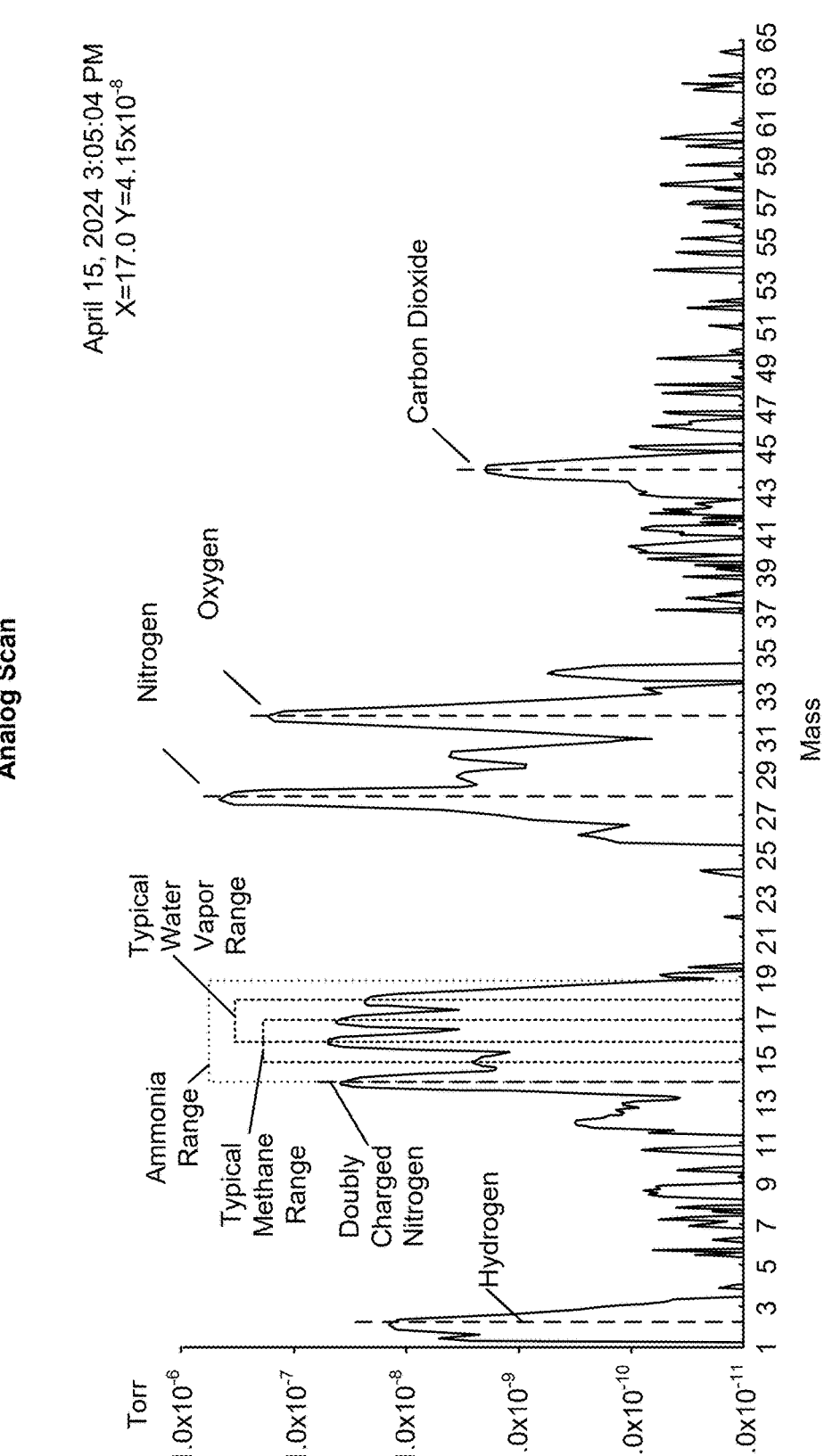
FIG. 5 is a graph of gas partial pressure compared to a mass/charge (m/z) spectrum of a fluid containing laboratory air (dominantly nitrogen, oxygen, and air) with admixtures of hydrogen and ammonia. Some embodiments relate to measuring fluids containing mixtures of hydrogen, helium, ammonia, hydrocarbon gases, nitrogen, carbon dioxide, various hydrogen-derived chemical species (e.g., dihydrogen sulfide, hydrogen cyanide), or other gases during drilling, testing, production, gathering, purification, and handling of the aforementioned chemical compounds.

In an embodiment, the correction of mass spectral interferences existing between m/z=15 and m/z=18 involves accurately quantifying known gas species that may be measured at those m/z values, then using known relative ionization efficiencies and mass spectral overlaps to subtract the possible interferences to improve or make possible the quantification of some gas species (e.g., ammonia). In an example embodiment, in the mass spectrometer when ammonia is ionized, approximately 0.26% of the total ammonia atoms is expected to be measured at mass m/z=18, approximately 52.49% is expected to be measured at m/z=17, approximately 41.99% is expected to be measured at m/z=16, and approximately 4.20% is expected to be measured at m/z=15. In this example, reliable quantification of ammonia requires removing interferences at either mass 18, 17, 16, or 15 (FIG. 5). Isotopologues of ammonia at m/z=19 and dehydrogenated (i.e., where all three hydrogen atoms have been cleaved off during ionization) ammonia at m/z=14 are also present but act as less consequential interferences for ammonia.

This embodiment can include using one or multiple stages of condensation/cryogenic separation to separate and remove interfering gas species or to accurately quantify the interfering gases enabling the direct quantification of ammonia. In an example embodiment, the largest portion of the total ammonia in a gas mixture is expected to be measured at m/z=17 in a quadrupole residual gas analyzer mass spectrometer. In this example, methane (approximately 0.55% of total methane molecules), and water vapor (approximately 17.11% of total water molecules) may also be measured in a mass spectrometer at m/z=17. This embodiment encompasses other possible gas species or compounds that, when ionized in a mass spectrometer, can interfere with m/z=17 (e.g., synthetic or less common gases or doubly charged dihydrogen sulfide).

In an embodiment, methane can be separated from ammonia and water vapor and be quantified when using condensation/cryogenic separation at liquid nitrogen temperatures (−196° C.) or tuned to achieve temperatures from −265° C. to +100° C. In this embodiment, methane can be separated from water vapor when the pressure and temperature conditions are within the range that methane remains in the gaseous state while water is in the condensed or frozen state, which can take place at relatively low vacuum pressures (e.g., 0.001-1 atmospheres) and modestly low temperatures (e.g., <~20° C.). This embodiment encompasses the tunable range of temperatures (e.g., tuned to achieve temperatures from −265° C. to +100° C.) that can separate methane from ammonia and water, methane from water, or other species in vacuum conditions that optimize the detection and measurement of gases using condensation/cryogenic separation for mud gas logging for the purposes of mud logging.

An embodiment of this invention includes the computer programming routines used to correct interferences between methane, ammonia, and water vapor. These routines use the data collected following the methods of using chemical sorbents or condensation/cryogenic separation to improve the detection limits of individual gas species in a split gas mixture as described above, and data reconciliation between multiple instruments.

An example embodiment for correcting the interferences for and quantifying ammonia may involve first removing the mass spectral interference from methane. This can be achieved, for example, utilizing the reliable relative abundances for methane measured in the second MS gas stream, which are then reconciled with data from the first MS gas stream to calculate an improved methane concentration within the bulk gas mixture. Once a corrected methane concentration is calculated, computer programming routines can automatically calculate the proportion of methane that would interfere at m/z=17 in the first MS gas stream based on the known ionization efficiencies of methane in a mass spectrometer.

The next step for correcting the interferences for and quantifying ammonia may involve similar calculations to remove the mass spectral interference from residual water vapor. In a simplified example, the abundance of residual water vapor may be measured at m/z=18 (approximately 74.40% of the total water vapor molecules are expected to be measured at this m/z) in the first MS gas stream and then used to calculate the proportion of water vapor that would interfere at m/z=17 based on the calculated ionization efficiencies of water vapor in a mass spectrometer. It is understood that in this simplified example a small proportion of the total ammonia will also be measured at m/z=18 (approximately 0.26% of the total ammonia molecules are expected to be measured at this m/z) and thus cannot be quantified as part of the total ammonia, instead being quantified as part of the water vapor component. While often negligible, similar processes can be applied to remove interferences from doubly charged dihydrogen sulfide (m/z=17) and/or other compounds that may be ionized and measured at m/z=17 if present in significant abundances. In this simplified example, after removing the possible interferences the remaining portion of the signal at m/z=17 represents the abundance of ammonia within the bulk gas mixture.

It is understood that the computer programming routines described above are examples and the actual data processing, reconciliation, interference corrections, and final abundance calculations may include multiple interference corrections and/or multiple stages of interference corrections as necessary to improve or make possible the detection of certain gas species, to include ammonia, based on the methods of chemical separation and/or condensation/cryogenic separation used in the measurement process. This may also involve multiple stages of data reconciliation depending on the abundances of gas species within the mixture and the methods used to quantify those gas species. For example, mass spectral inferences may exist not only due to variable ionization efficiencies but also overlap from multiply-substituted isotopologues of individual gas species, which may be quantified separately with other techniques and instrumentation such as isotope ratio mass spectrometers.

An embodiment of this invention includes the real-time detection and quantification of ammonia for the purposes of mud logging utilizing mass spectrometry. As described herein, the inventors have determined a likelihood that drill bit metamorphism obscures mud gas logging because some fraction of hydrogen in situ or in the borehole is converted into ammonia during the drilling process. Accordingly, to develop an accurate profile of hydrogen potential and indicators during mud gas logging requires understanding the relative abundances of ammonia and hydrogen.

A further embodiment of this invention includes the monitoring, detecting, and quantifying of ammonium (NH₄+) ions present in drilling fluid (i.e., mud fluid stream) returns for the purposes of mud gas logging. In this embodiment, field portable measuring devices, such as multiparameter meters, can be used to measure ammonium ions in the mud fluid stream using an ion-selective electrode probe or other measuring device. In this embodiment, this measurement can take place at the location of circulated drilling fluid and cuttings (e.g., possum belly, shaker, or agitator where drilling fluids are separated) but can also take place at a location away from the drilling fluid circulating equipment if the drilling fluid is first collected into a vessel for measurement elsewhere.

In aqueous solutions, ammonia dissolves in water as ammonium as a function of (and eventually influenced by) pH. In solutions of pH >11, nearly all ammonium is converted to ammonia gas. In solutions of pH <8, nearly all ammonia is converted to dissolved ammonium. Within slightly to moderately basic solutions (pH between 8 and 11), both ammonia and ammonium will co-exist in differing but predictable proportions. During drilling operations, it is common for the pH of the drill mud to be less than 11 (where ammonia will convert to ammonium). Therefore, to accurately quantify the amount of ammonia introduced into the drilling mud from the penetrated rock, ammonium must also be monitored using a mud logging system. Legacy mud logging systems are not equipped to detect or quantify ammonium for the purposes of detecting and quantifying ammonia during mud gas logging.

Another embodiment discloses methods for detecting, monitoring, and quantifying the composition of hydrogen, helium, ammonia, hydrocarbon gases, nitrogen, carbon dioxide, other gases, and hydrogen derivatives during the gathering, purification, and handling of these compounds. This embodiment encompasses onsite determination of separation efficiency for various impurities and carbon-containing intensive species, including hydrocarbons or carbon dioxide.

The systems disclosed herein may include a computing device having at least one processor and a memory storage storing data and one or more operational programs thereon for implementing certain steps of the methods disclosed herein. The memory storage (e.g., a non-transitory memory storage medium) is in electronic communication with the processor in electronic communication. The system includes a communication network in electronic communication with the computing device. The computing device may include one or more servers, one or more computers (e.g., desk-top computer, lap-top computer), or one or more mobile computing devices (e.g., smartphone, tablet, etc.). The processor of the computing device includes hardware for executing instructions (e.g., instructions for carrying out one or more portions of any of the methods disclosed herein), such as those making up an operational program. The processor is configured to read and execute operational programs stored in the memory storage.

The memory storage of the computing device may include one or more of volatile and non-volatile memories, such as Random Access Memory (RAM), Read Only Memory (ROM), a solid state disk (SSD), Flash, Phase Change Memory (PCM), or other types of data storage. The memory storage may be internal or distributed memory. The one or more operational programs stored in the memory storage may include machine readable and executable instructions for performing any of the portions of the methods disclosed herein. For example, the operational programs may include instructions for reading raw data and processing the outputs to produce corrected results, as disclosed herein. The operational programs may include instructions to quantify an amount of geologic hydrogen in a gas stream, quantify an amount of geologic hydrogen derivatives in the gas stream, correlate the amount of geologic hydrogen derivatives in the gas stream to an estimated amount of source hydrogen, and generate the enhanced quantification of hydrogen in the gas stream based on the amount of geologic hydrogen in the gas stream and the estimated amount of source hydrogen. The memory storage also has a data storage therein for storing one or more sets of data, outputs of the methods disclosed herein, or any other digital information used in the methods disclosed herein.

Drill Bit Metamorphism

An embodiment of this invention involves the identification of drill bit metamorphism (i.e., thermal degradation of the steel or metallic components of the drill bit and/or in situ changes to the chemical composition of gases in the wellbore caused by the drilling process) utilizing gas geochemical indicators detected during mud gas logging. A drill bit may degrade as a result of, for example, extended use or if the drilling operation encounters a subsurface interval composed of particularly dense or hard material, including but not limited to igneous rocks. The degradation of a drill bit can lead to a reaction between the steel or other alloys that are used in the drill bit, water or formation brine, pulverized rock resulting from the drilling, and drilling fluids with the high heat/friction induced during drilling. This process can lead to the artificial generation and release of, for example, hydrogen, carbon monoxide, carbon dioxide, carbon disulfide, sulfur dioxide, dihydrogen sulfide, abiogenic methane, other hydrocarbons (e.g., if using oil-based drilling mud or in the presence of biocides and other additives), among other gases. In contrast, naturally occurring fluids originating in the subsurface including hydrogen, helium, nitrogen, hydrocarbons, and carbon dioxide have characteristic geochemical fingerprints that would allow the distinction between drill bit metamorphism and subsurface fluids during mud gas logging. For example, drill bit metamorphism would not release helium in addition to the aforementioned gas species as helium cannot be generated by the same processes listed above, but helium would be present in variable quantities in subsurface fluids because it is generated by the radioactive decay of uranium and thorium in crustal materials. Further, relative abundances between compounds such as hydrogen, helium, methane, other hydrocarbons, nitrogen, argon, and carbon monoxide, carbon disulfide, sulfur dioxide, carbon dioxide, among others, can be used to identify subsurface-originating fluids.

Accordingly, some example systems and methods contemplated herein may be used to identify drill bit metamorphism in the wellbore. For example, the profile of a gas sample taken over time can demonstrate changes in the abundances of gases that reveal the artificial generation of a particular gas. The gases in the gas stream include one or more of hydrogen, carbon monoxide, carbon dioxide, carbon disulfide, sulfur dioxide, dihydrogen sulfide, abiogenic methane, and other hydrocarbons.

To identify the artificial generation of a particular gas, a relative abundance in the gas sample of a reference gas to the particular gas is calculated. The relative abundance may then be compared to a predefined threshold or criteria consistent with the natural geochemical fingerprint of the geological system. If the relative abundance deviates from the predefined threshold, then it may be determined that there has been artificial generation of the gas (e.g., drill bit metamorphism). If the relative abundance is consistent with the predefined threshold, then drill bit metamorphism affecting relative quantities of the particular gas and the reference gas is unlikely to have occurred.

In some embodiments, the reference gas is hydrogen, helium, methane, a hydrocarbon, nitrogen, argon, carbon monoxide, carbon disulfide, sulfur dioxide, or carbon dioxide.

Conclusion

It is noted that there is no requirement to provide or address the theory underlying the novel and groundbreaking systems, methods, performance or other beneficial features and properties that are the subject of, or associated with, embodiments of the present disclosure. Nevertheless, various theories are provided in this specification to further advance the art in this critical area, and in particular the important area of hydrogen, dihydrogen sulfide, carbon dioxide, and helium exploration, production and downstream conversion or utilization. These theories put forth in this specification, and unless expressly stated otherwise, in no way limit, restrict or narrow the scope of protection to be afforded the claimed embodiments. It is further understood that the present disclosure may lead to new, and heretofore unknown theories to explain the conductivities, drainages, resource production, chemistries, and function-features of embodiments of the methods, articles, materials, devices, and system of the present disclosure and that such later developed theories shall not limit the scope of protection afforded the present disclosure. Other embodiments than those specifically disclosed herein may be included without departing from its spirit or essential characteristics.

Further, the various embodiments of devices, systems, activities, methods, and operations set forth in this specification may be used with each other in different and various combinations. Thus, the configurations provided in the various embodiments of this specification may be used with each other. For example, the components of an embodiment having A, A', and B and the components of an embodiment having A", C, and D can be used with each other in various combinations (e.g., A, C, D, and A; A", C, and D; etc.) in accordance with the teaching of this specification. Thus, the scope of protection afforded by the present inventions should not be limited to a particular embodiment, configuration or arrangement that is set forth in a particular embodiment, example, or in an embodiment in a particular Figure.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for enhanced quantification of hydrogen from a wellbore, the method comprising:

receiving a mud fluid stream from the wellbore, wherein the mud fluid stream includes geologic hydrogen and geologic hydrogen derivatives;

separating one or more gases other than hydrogen from the mud fluid stream to produce a gas stream;

quantifying an amount of geologic hydrogen in the gas stream;

quantifying an amount of geologic hydrogen derivatives in the gas stream;

correlating the amount of geologic hydrogen derivatives in the gas stream to an estimated amount of source hydrogen; and generating the enhanced quantification of hydrogen in the gas stream based on the amount of geologic hydrogen in the gas stream and the estimated amount of source hydrogen.

2. The method of claim 1, wherein the geologic hydrogen derivatives include ammonia and the method further comprises:

quantifying an amount of ammonium in the mud fluid stream; and measuring an amount of ammonia present in the gas stream, wherein quantifying the amount of geologic hydrogen derivatives in the gas stream is based on the amount of ammonium in the mud fluid stream and the amount of ammonia present in the gas stream.

3. The method of claim 2, wherein quantifying the amount of ammonium in the mud fluid stream comprises applying an ion-selective electrode probe to the mud fluid stream to measure the amount of ammonium.

4. The method of claim 2, further comprising:

separating methane from the gas stream, wherein measurement of the amount of ammonia present in the gas stream occurs after separating methane from the gas stream.

5. The method of claim 2, further comprising:

separating water vapor from the gas stream, wherein measurement of the amount of ammonia present in the gas stream occurs after separating water vapor from the gas stream.

6. The method of claim 1, wherein the geologic hydrogen derivatives include ammonia, hydrogen cyanide, dihydrogen sulfide, one or more hydrocarbons, or a combination thereof.

7. The method of claim 1, wherein the geologic hydrogen derivatives include water, a water isotope, or a combination thereof.

8. The method of claim 1, further comprising:

separating a water isotope from the gas stream, wherein measurement of the amount of ammonia present in the gas stream occurs after separation the water isotope from the gas stream.

9. The method of claim 1, wherein the step of quantifying an amount of geologic hydrogen derivatives in the gas stream comprises directing the gas stream to a gas chromatography column and a thermal conductivity detector.

10. The method of claim 9, wherein the gas chromatography column is packed with ethylene glycol-dimethacrylate.

11. A chemical instrumentation system for enhanced quantification of geologic hydrogen in a gas stream from a wellbore, the chemical instrumentation system comprising:

gas stream tubing configured to:

receive a mud fluid stream from the wellbore, wherein the mud fluid stream includes geologic hydrogen and geologic hydrogen derivatives, and split a gas stream from the mud fluid stream;

means for separating one or more gases other than hydrogen from the mud fluid stream to produce the gas stream;

a gas chromatography configuration coupled to the gas stream, the gas chromatography configuration including:

a gas chromatography column configured to receive the gas stream, and one of a thermal conductivity detector or a photoionization detector coupled to the gas chromatography column and configured to quantify gas species eluted from the gas chromatography column, wherein the gas species includes the geologic hydrogen and the geologic hydrogen derivatives; and a computing device having a processor and memory storage operably coupled to the processor, the memory storage having one or more computer programming routines, the processor configured to read and execute the one or more computer programming routines, wherein the one or more computer programming routines include machine readable and executable instructions to:

quantify an amount of geologic hydrogen in the gas stream;

quantify an amount of geologic hydrogen derivatives in the gas stream;

correlate the amount of geologic hydrogen derivatives in the gas stream to an estimated amount of source hydrogen; and generate the enhanced quantification of hydrogen in the gas stream based on the amount of geologic hydrogen in the gas stream and the estimated amount of source hydrogen.

12. The chemical instrumentation system of claim 11, wherein the gas chromatography configuration includes a separation component coupled to the gas stream and configured to separate water vapor from the gas stream prior to measuring the gas species of the gas stream.

13. The chemical instrumentation system of claim 11, wherein the geologic hydrogen derivatives include ammonia, hydrogen cyanide, dihydrogen sulfide, one or more hydrocarbons, water, water isotopes, or combinations thereof.

14. The chemical instrumentation system of claim 11, wherein the geologic hydrogen derivatives include ammonia, and the one or more computer programming routines further include machine readable and executable instructions to:

quantify an amount of ammonium in the mud fluid stream; and measure an amount of ammonia present in the gas stream;

wherein quantifying the amount of geologic hydrogen derivatives in the gas stream is based on the amount of ammonium in the mud fluid stream and the amount of ammonia present in the gas stream.

15. The chemical instrumentation system of claim 14, further comprising an ion-selective electrode probe, and wherein quantifying the amount of ammonium in the mud fluid stream comprises receiving a measurement of the amount of ammonium from the ion-selective electrode probe applied to the mud fluid stream.

16. The chemical instrumentation system of claim 14, wherein the gas chromatography configuration includes a separation component coupled to the gas stream and configured to separate methane from the gas stream prior to measuring the ammonia present in the gas stream.

17. The chemical instrumentation system of claim 14, wherein the gas chromatography configuration includes a separation component coupled to the gas stream and configured to separate water vapor from the gas stream prior to measuring the ammonia present in the gas stream.

18. The chemical instrumentation system of claim 14, wherein the gas chromatography configuration includes a separation component coupled to the gas stream and configured to separate a water isotope from the gas stream prior to measuring the ammonia present in the gas stream.

\*  \*  \*  \*  \*